(12) United States Patent
Wang et al.

(10) Patent No.: US 11,131,029 B2
(45) Date of Patent: Sep. 28, 2021

(54) SYSTEMS, DEVICES, AND METHODS EMPLOYING ELECTROCHEMICAL PROCESSING OF HYDROFLUOROOLEFINS

(71) Applicant: University of Maryland, College Park, College Park, MD (US)

(72) Inventors: Chunsheng Wang, Silver Spring, MD (US); Ye Tao, Rockville, MD (US); K. Reinhard Radermacher, Silver Spring, MD (US); Yunho Hwang, Ellicott City, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 161 days.

(21) Appl. No.: 16/201,995

(22) Filed: Nov. 27, 2018

(65) Prior Publication Data
US 2019/0161870 A1 May 30, 2019

Related U.S. Application Data

(60) Provisional application No. 62/590,916, filed on Nov. 27, 2017.

(51) Int. Cl.
*C25B 9/10* (2006.01)
*C25B 9/23* (2021.01)
(Continued)

(52) U.S. Cl.
CPC ............ *C25B 9/23* (2021.01); *C07C 21/18* (2013.01); *C25B 13/08* (2013.01); *C25B 15/02* (2013.01);
(Continued)

(58) Field of Classification Search
CPC ........... C25B 9/10; C25B 13/08; C25B 15/08; C25B 15/02; C07C 21/18; H01M 4/9041;
(Continued)

(56) References Cited

U.S. PATENT DOCUMENTS 6,387,230 B1 5/2002 Murphy et al.
7,846,604 B2 12/2010 Highgate et al.
(Continued)

OTHER PUBLICATIONS

Adams et al., "A carbon dioxide tolerant aqueous-electrolyte-free-anion-echange membrane alkaline fuel cell," *ChemSusChem*, Feb. 2008, 1(1-2): pp. 79-81.
(Continued)

*Primary Examiner* — Arun S Phasge
(74) *Attorney, Agent, or Firm* — RowanTree Law Group, PLLC; Frederick F. Rosenberger

(57) ABSTRACT

Hydrofluoroolefin (HFO) fluid can be transported through an electrochemical device, which has a proton exchange membrane (PEM) disposed between a pair of gas-permeable electrodes that include respective catalysts. At an inlet side, the catalyst facilitates reaction of HFO with hydrogen carrier gas. The resulting cation is transported across PEM in the presence of an electric field applied to the electrodes. At an outlet side, the catalyst of the opposing electrode facilitates dissociation of the cation back into HFO and hydrogen. In some embodiments, the transported HFO has a higher pressure than that before the electrochemical device. In some embodiments, the electrochemical device can be operated in reverse to expand HFO fluid and/or to recapture power. The electrochemical device can thus be used as a compressor or expander for vapor-phase HFO or as a pump or expander for liquid-phase HFO, for example, in power generation or heating/cooling cycles.

20 Claims, 13 Drawing Sheets

(51) Int. Cl.
C07C 21/18 (2006.01)
C25B 13/08 (2006.01)
C25B 15/08 (2006.01)
C25B 15/02 (2021.01)
H01M 4/90 (2006.01)
H01M 8/0221 (2016.01)
H01M 8/04701 (2016.01)
H01M 8/04537 (2016.01)
H01M 8/04746 (2016.01)
H01M 8/0284 (2016.01)

(52) U.S. Cl.
CPC ........... C25B 15/08 (2013.01); H01M 4/9041 (2013.01); H01M 8/0221 (2013.01); H01M 8/0284 (2013.01); H01M 8/04537 (2013.01); H01M 8/04708 (2013.01); H01M 8/04753 (2013.01)

(58) Field of Classification Search
CPC ........... H01M 8/0221; H01M 8/04708; H01M 8/04537; H01M 8/04753; H01M 8/0284; Y02E 60/50; Y02C 20/30
See application file for complete search history.

(56) References Cited

U.S. PATENT DOCUMENTS

| | | |
|---|---|---|
| 8,627,671 B2 | 1/2014 | Bahar |
| 8,640,492 B2 | 2/2014 | Bahar |
| 8,769,972 B2 | 7/2014 | Bahar |
| 9,005,411 B2 | 4/2015 | Bahar et al. |
| 9,151,283 B2 | 10/2015 | Bahar et al. |
| 9,457,324 B2 | 10/2016 | Bahar et al. |
| 9,599,364 B2 | 3/2017 | Bahar et al. |
| 9,738,981 B2 | 8/2017 | Naugler et al. |
| 9,909,224 B2 | 3/2018 | Bahar |
| 10,087,532 B2 | 10/2018 | Bahar et al. |
| 2002/0127474 A1* | 9/2002 | Fleischer ............ H01M 2/1653 429/309 |
| 2004/0211679 A1 | 10/2004 | Wong et al. |
| 2011/0133308 A1 | 6/2011 | Chan et al. |
| 2015/0241091 A1 | 8/2015 | Bahar |
| 2016/0341449 A1 | 11/2016 | Bahar et al. |
| 2017/0362720 A1 | 12/2017 | Bahar et al. |

OTHER PUBLICATIONS

Agmon, N., "The grotthuss mechanism," *Chemical Physics Letters*, Oct. 1995, 244(5-6): pp. 456-62.
Ahammed et al., "Thermoelectric cooling of electronic devices with nanofluid in a multiport minichannel heat exchanger," *Experimental Thermal and Fluid Science*, Jun. 2016, 74: pp. 81-90.
Barbir, F., *PEM fuel cells: theory and practice*, Elsevier Academic Press, 2005 (449 pages).
Bedbak et al., "Performance analysis of a compressor driven metal hydride cooling system," *International Journal of Hydrogen Energy*, Aug. 2005, 30(10): pp. 1127-37.
Chen et al., "Hydroxide solvation and transport in anion exnchange membranes," *Journal of the American Chemical Society*, Jan. 2016, 138(3): pp. 991-1000.
Chung et al., "Carbon film-coating 304 stainless steel as PEMFC bipolar plate," *Journal of Power Sources*, Jan. 2008, 176(1): pp. 276-81.
Dais Analytical Corporation, "Membrane dehumidification enabling alternative cooling strategies in humid envrionments," Slide deck [online]. Advanced Research Projects Agency—Energy (ARPA-E) Summit, 2013 [retrieved on Jan. 4, 2021]. Retrieved from the Internet: <URL: http://www.arpae-summit.com/paperclip/exhibitor_docs/13AE/Dais_Analytic_Corporation_104.pdf>. (11 pages).

Dekel, D., "Review of cell performance in anion exchange membrane fuel cells," *Journal of Power Sources*, Jan. 2018, 365: pp. 158-69.
Disalvo, F., "Thermoelectric cooling and power generation," *Science*, Jul. 1999, 285(5428): pp. 703-06.
Eberle et al., "Fuel cells electric vehicles and hydrogen infrastructure: status 2012," *Energy & Environmental Science*, Jul. 2012, 5(10): pp. 8780-98.
Gardner et al., "Electrochemical separation of hydrogen from reformate using PEM fuel cell technology," *Journal of Power Sources*, Jun. 2007, 171(2): pp. 835-41.
Garrity et al., "A flow boiling microchannel evaporator plate for fuel cell thermal management," *Heat Transfer Engineering*, Oct. 2007, 28(10): pp. 877-84.
Gerlach, D., "Experimental verification off electroosmotic dehumidification with Nafion and plaster-silica gel membranes," *International Refrigeration and Air Conditional Conference at Purdue*, 2008, Paper No. 862 (9 pages).
Grigoriev et al., "Description and characterization of an electrochemical hydrogen compressor/concentrator based on solid polymer electrolye technology," *International Journal of Hydrogen Energy*, Mar. 2011, 36(6): pp. 4148-55.
Halseid et al., "Effect of ammonia on the performance of polymer elextrolye membrane fuel cells," *Journal of Power Sources*, Mar. 2006, 154(2): pp. 343-50.
Hibino et al., "Oxygen rocking aqueous batteries utilizing reversible *topotactic* oxygen insertion/extraction in iron-based perovskite oxides $Ca_{1-x}La_xFeO_{3-\delta}$," *Scientific Reports*, Aug. 2012, 2:601 (4 pages).
Hopkins et al., "Hydrogen compression characteristics of a dual stage thermal compressor system utilizing $LaNi_5$ and $Ca_{0.6}Mm_{0.4}Hi_5$ as the working metal hydrides,"*International Journal of Hydrogen Energy*, Jun. 2010, 35(11): pp. 5693-702.
Jung et al., "An experimental approach to investigate the transport of ammonia as a fuel contaminant in proton exchange membrane fuel cells," *Journal of Power Sources*, Feb. 2015, 275: pp. 14-21.
Kim et al., "Compressor-driven metal-hydride heat pumps," *Applied Thermal Engineering*, Jun. 1997, 17(6): pp. 551-60.
Luo et al., "An acrylate-polymer-based electrolye membrane for alkaline fuel cell appplications," *ChemSusChem*, Nov. 2011, 4(11): pp. 1557-60.
Luo et al., "Electro-osmotic drag coefficient and proton conductivity in Nafion® membrane for PEMFC," *International Journal of Hydrogen Energy*, Apr. 2010, 35(7): pp. 3120-24.
Magnetto et al., "A metal hydride mobile air conditioning system," *SAE Transactions*, Jan. 2006, 115(6): pp. 1150-59.
Matian et al., "Model based design and test of cooling plates for an air-cooled polymer electrolye fuel cell stack," *International Journal of Hydrogen Energy*, 2011, 36(10): pp. 6051-66.
Mazumdar et al., "Performance of compressor driven metal hydride cooling systems under different operating conditions," *International Conditioning Conference*, Jul. 2004, Paper No. 721 (9 pages).
Mefford et al., "Anion charge storage through oxygen intercalation in $LaMnO_3$ perovskite pseudocapacitor electrodes," *Nature Materials*, 2014, 13(7): pp. 726-32.
Muthukumar et al., "Metal hydride based heating and cooling systems: A review," *International Journal of Hydrogen Energy*, Apr. 2010, 35(8): pp. 3817-31.
Odabaee et al., "Metal foam heat exchangers for thermal management of fuel cell systems—An experimental study," *Experimental Thermal and Fluid Science*, 2013, 51: pp. 214-19.
Onda et al., "Seperation and compression characteristics of hydrogen by use of proton exchange membrane," *Journal of Power Sources*, Jan. 2007, 164(1): pp. 1-8.
Park et al., "The development of compressor-driven metal hydride heat pump (CDMHHP) system as an air conditioner," *International Journal of Hydrogen Energy*, Sep. 2002, 27(9): pp. 941-44.
Park et al., "The operating characteristics of the compressor-driven metal hydride heat pump system," *International Journal of Hydrogen Energy*, Jul. 2001, 26(7): pp. 701-06.
Pennline et al., "Separation of $CO_2$ from flue gas using electrochemical cells," *Fuel*, Jun. 2010, 89(6): pp. 1307-14.

(56) References Cited

OTHER PUBLICATIONS

Possamai et al., "Miniature vapor compression system," *International Refrigeration and Air Conditioning Conference*, Jul. 2008, Paper No. 963 (9 pages).
Pozio et al., "Bipolar plate meterials for PEMFCs: a conductivity and stability study," *Journal of Power Sources*, May 2008, 179(2): pp. 631-39.
Qian et al., "Not-in-kind cooling technologies: A quantiative comparison of regrigerants and system performance" *International Journal of Refrigeration*, Feb. 2016, 62: pp. 177-92.
Rohland et al., "Electrochemical hydrogen compressor," *Electrochimica Acta*, Aug. 1998, 43(24): pp. 3841-46.
Sandrock, G., "A panoramic overview of hydrogen storage alloys from a gas reaction point of view," *Journal of Alloys and Compounds*, Dec. 1999, 293: pp. 877-88.
Schmidt, et al., "Low-coast air-cooled PEFC stacks," *Journal of Power Sources*, Mar. 2002, 105(2): pp. 243-49.
Sedlak et al., "Hydrogen recovery and purification using the solid polymer electrolysis cell," *International Journal of Hydrogen Energy*, Jan. 1981, 6(1): pp. 45-51.
Shafiee et al., "Different reactor and heat exchanger configurations for metal hydride hydrogen storage systems—a review," *International Journal of Hydrogen Energy*, 2016, 41(22): pp. 9462-70.
Soto et al., "Effect of transient ammonia concentrations on PEMFC performance," *Electrochemical and Solid State Letters*, Apr. 2003, 6(7): pp. A133-35.
Stolaroff, J. "Carbonate solutions for carbon capture: A summary," Lawrence Livermore National Laboratory (LLNL), Oct. 2013, LLNL-TR-644894 (19 pages).
Ströbel et al., "The compression of hydrogen in an electrochemical cell based on a PE fuel cell design," *Journal of Power Sources*, Mar. 2002, 105(2): pp. 208-15.
Suzuki et al., "Fundamental studies on direct ammonia fuel cell employing anion exchange membrane," *Journal of Power Sources*, Jun. 2012, 208: pp. 257-62.
Tao et al., "Electrochemical ammonia compression," *Chemical Communications,* 2017, 53(41): pp. 5637-40.
Tao et al., "Electrochemical compressor driven metal hydride heat pump," *International Refrigeration*, Dec. 2015, 60: pp. 278-88.
Tao et al., "Performance investigation on electrochemical compressor with ammonia," *23$^{rd}$International Compressor Engineering Conference*, Jul. 2016, Paper No. 2469 (7 pages).
Tao et al., "The integration of ammonia electrochemical compressor in vapor compression system," *12$^{th}$Heat Pump Conference*, May 2017, Paper No. O.4.9.1 (6 pages).
Tao, Y., "Electrochemical compression with ion exchange membranes for air conditioning, refrigeration, and other related applications," PhD Dissertation, Digital Repository at the University of Maryland [online], 2017 [retrieved on Aug. 11, 2018]. Retrieved from the Internet: <URL: http://hdl.handle.net/1903/20427>. (147 pages).
Unlu et al., "Anion exchange membrane fuel cells: experimental comparison of hydroxide and carbonate conductive ions," *Electrochemical and Solid State Letters*, Jan. 2009, 12(3): pp. B27-30.
Varcoe et al., "Anion-exchange membranes in electrochemical energy systems," *Energy & Environmental Science*, 2014, 7(10): pp. 3135-91.

Wang et al., "Investigation of potential benefits of compressor cooling," *Applied Thermal Engineering*, Oct. 2008, 28(14-15): pp. 1791-97.
Weng et al., "Electrochemical $CO_2$ reduction to hydrocarbons on a heterogenous molecular CU catalyst in aqueous solution", *Journal of the American Chemical Society*, 138(26): pp. 8076-79.
Zhang et al., "A critical review of cooling techniques in proton exchange membrane fuel cell stacks," *International Journal of Hydrogen Energy*, Feb. 2012, 37(3): pp. 2412-29.
Choi et al., "Thermodynamics and proton transport in Nafion: II. Proton diffusion mechanisms and conductivity," *Journal of the Electrochemical Society*,Feb. 2005, 152(3): pp. E123-30. (8 pages).
Chugh et al., "Hybrid Membrane-based Ionic Liquid Absorption Cycle for Water Heating Dehumidification and Cooling," *12$^{th}$IEA Heat Pump Conference*, 2017, Paper No. O4.4.3. (10 pages).
Lim et al., "Cycle characteristics of water-based membrane heat pump in cooling mode operation," *Asian Conference on Thermal Sciences*, 2017, Paper No. ACTS-P00669. (3 pages).
Moton et al., "Advances in electrochemical compression of hydrogen," *Proceedings ofo the ASME 2014 12th International Conference on Fuel Cell Science, Engineering and Technology*, 2014, Paper No. 2014-6641. (10 pages).
Ridgdon et al., "Reaction dependent transport of carbonate and bicarbonate through anion exhange membranes in electrolysis and fuel cell operations," *ECS Transactions*, Dec. 2015, 69(33): pp. 1-9.
Sathe et al., "Design Optimization of Elextrostatically Actuated Miniature Compressors for Electronics Cooling," *International Compressor Engineering Conference*, 2008, Paper No. 1865. (11 pages).
Takeda et al., "Metal hydride air-conditioning" in *Energy Carriers and Convesion Systems*, Volume II. 2009. Encyclopedia of Life Support Systems (EOLSS) Publishers Co. Ltd., Oxford, UK, pp. 249-63. (17 pages).
Tao et al., "Experimental investigation on elextrochemical ammonia compressor,"*12th International Institute of Refrigeration (IIR) Gustav Lorentzen Natural Working Fluids Conference*, 2016, Paper No. 1016. (8 pages)
Tao et al., "Experimental syudy on electrochemical compression of ammonia and carbon dioxide for vapor compression refrigeration system," *International Journal of Refrigeration*, 2019, 104: pp. 180-88. (9 pages).
Urbie et al., "Effect of ammonia as potential fuel impurity on proton exchange membrane fuel cell performance," *Journal of the Electrochemical Society*, Jan. 2002, 149(3): A293-96. (4 pages).
Vega et al., "Carbonate selective $Ca_2Ru_2\,O_{7-y}$Pyrochlore enabling room temperature carbonate fuel cells: I. Synthesis and physical characterization," *Journal of The Electrochemical Society*, Dec. 2011, 159(1): pp. B12-17 (6 pages).
Vega et al., "Carbonate selective $Ca_2Ru_2\,O_{7-y}$Pyrochlore enabling room temperature carbonate fuel cells: II. Verification of carbonate cycle and electrochemical performance," *Journal of The Electrochemical Society*, 2012, 159(1): pp. B19-24. (6 pages).
Zhong et al., "Metal-hydride adsoprtion systems for space conditioning in commercial and residential buildings," *Proceedings of the ASME International Mechanical Engineering Congress and Exposition*, Nov. 2014, Paper No. V08AT10A080. (9 pages).

* cited by examiner

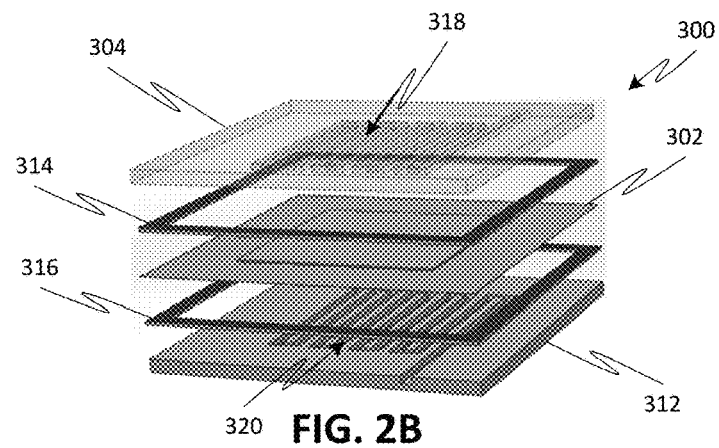
FIG. 2B
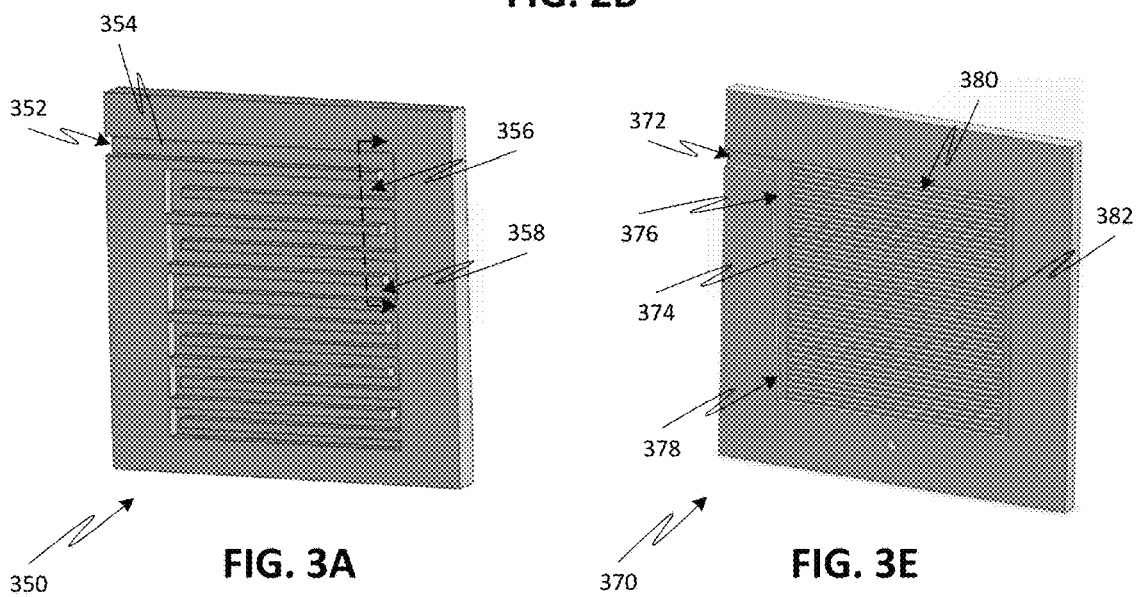
FIG. 3A
FIG. 3E
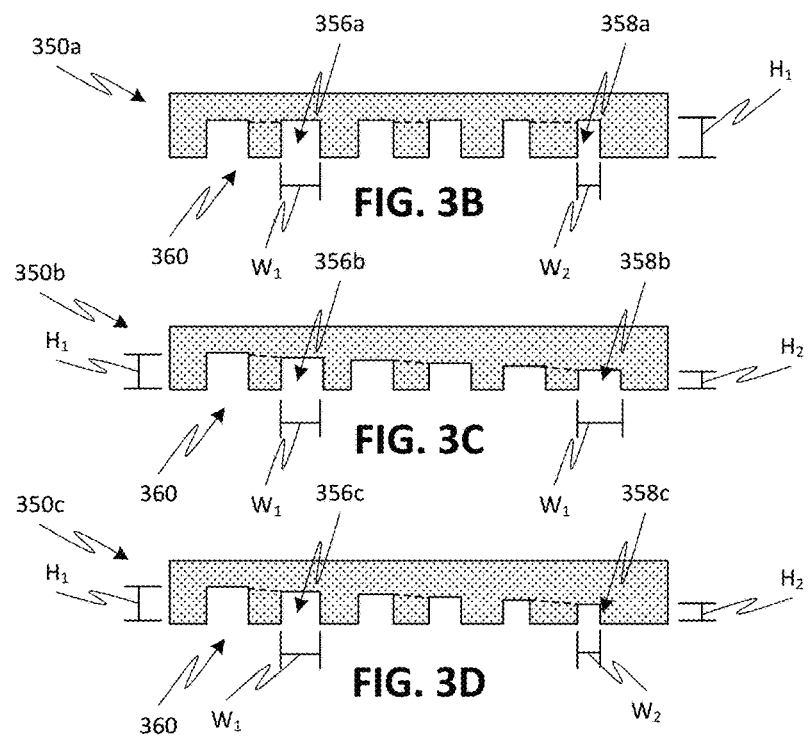
FIG. 3B
FIG. 3C
FIG. 3D

SYSTEMS, DEVICES, AND METHODS EMPLOYING ELECTROCHEMICAL PROCESSING OF HYDROFLUOROOLEFINS

CROSS-REFERENCE TO RELATED APPLICATIONS

The present application claims the benefit of U.S. Provisional Application No. 62/590,916, filed Nov. 27, 2017, which is hereby incorporated by reference herein in its entirety.

FIELD

The present disclosure relates generally to thermodynamic processing, and more particularly, to systems, devices, and methods employing electrochemical processing (e.g., pumping, compression, or expansion) of hydrofluoroolefins (HFO).

SUMMARY

Embodiments of the disclosed subject matter pump an HFO fluid and/or alter a pressure thereof via an electrochemical device. The electrochemical device combines HFO fluid with protons from a hydrogen carrier gas to form cations and then transports the cations through a proton exchange membrane. The proton exchange membrane can be disposed between opposing electrodes, which may include respective catalysts that facilitate the reaction of the HFO fluid with the hydrogen carrier gas. For example, the electrochemical process performed by the electrochemical device can be a part of a heating/cooling system or a power generation system employing HFO as a working fluid, such as a vapor compression cycle, an organic Rankine cycle (ORC), and a Brayton cycle.

In some embodiments, the electrochemical device is operated as a compressor, whereby an electric field applied to the electrodes causes transport of the HFO fluid through the proton exchange membrane to provide a higher pressure HFO fluid at an outlet of the electrochemical device. In other embodiments, the electrochemical device is operated as an expander or power harvesting device, whereby the electrodes capture power generated by transport of the HFO fluid through the proton exchange membrane and the HFO fluid at the outlet of the electrochemical device has a lower pressure. In still other embodiments, the electrochemical device operates as a pump that moves the HFO fluid in a liquid phase or partially liquid phase.

In one or more embodiments, a system comprises an electrochemical device and a fluid circulating in the system. The electrochemical device comprises a proton exchange membrane disposed between a pair of electrodes. The electrochemical device is constructed to transport the fluid through the proton exchange membrane, in the presence of an electric field applied between the pair of electrodes, via a combination of the fluid with a carrier gas. Each of the pair of electrodes comprises a respective catalyst. The carrier gas comprises $H_2$, and the fluid comprises a hydrofluoroolefin (HFO).

In one or more embodiments, a method comprises applying an electric field between first and second electrodes. The first electrode is on an inlet side of a proton exchange membrane of an electrochemical module, and the second electrode is on an outlet side of the proton exchange membrane. The outlet side is opposite to the inlet side. The method further comprises, at the inlet side of the proton exchange membrane, combining a fluid and a carrier gas. The method also comprises, under influence of the applied electric field, transporting the combined fluid and carrier gas through the proton exchange membrane to the outlet side, and, at the outlet side of the proton exchange membrane, dissociating the transported combination to re-form the fluid and carrier gas. The first and second electrodes comprise a respective catalyst. The carrier gas comprises $H_2$, and the fluid comprises an HFO.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. Where applicable, some elements may be simplified or otherwise not illustrated in order to assist in the illustration and description of underlying features. Throughout the figures, like reference numerals denote like elements.

FIG. 2B is an exploded perspective view of an electrochemical device, according to one or more embodiments of the disclosed subject matter.

FIG. 3A is a perspective view of an outlet face of an exemplary gas inlet manifold of an electrochemical device, according to one or more embodiments of the disclosed subject matter.

FIG. 3B is a cross-sectional view of an inlet flow channel of the gas inlet manifold having a first exemplary geometry, according to one or more embodiments of the disclosed subject matter.

FIG. 3C is a cross-sectional view of an inlet flow channel of the gas inlet manifold having a second exemplary geometry, according to one or more embodiments of the disclosed subject matter.

FIG. 3D is a cross-sectional view of an inlet flow channel of the gas inlet manifold having a third exemplary geometry, according to one or more embodiments of the disclosed subject matter.

FIG. 3E is a perspective view of an inlet face of an exemplary gas outlet manifold of an electrochemical device, according to one or more embodiments of the disclosed subject matter.

DETAILED DESCRIPTION

Embodiments of the disclosed subject matter relate to electrochemical processing of a fluid comprising hydrofluoroolefins (HFOs). HFOs are unsaturated compounds of hydrogen, fluorine, and carbon that have relatively low global warming potential (GWP) (e.g., a GWP$\leq$5). Exemplary HFOs include, but are not limited to, 2,3,3,3-tetrafluoropropene (HFO-1234yf or R-1234yf), 1,3,3,3-tetrafluoropropene (HFO-1234ze, HFO-1234ze(E), or R-1234ze), 1-chloro-3,3,3-trifluoropropene (HFO-1233zd, HFO-1233zd(E), or R-1233zd), and 1,1,1,4,4,4-hexafluor-2-buten (HFO-1336mzz(Z) or R-1336mzz(Z)).

In the disclosed systems, one or more pressure processes (i.e., pumping, compression, or expansion) can be accomplished using an electrochemical device, which electrochemically transports the fluid facilitated by a carrier gas rather than using moving parts or valving. When operated in a pumping or compression mode, the electrochemical device transports cations of the HFO fluid through a proton exchange membrane in the presence of an electric field. When the HFO is in a vapor phase, the transport can be such that a pressure of the HFO fluid on an outlet side of the membrane is higher than on an inlet side. Appropriate thermal management of the electrochemical device can result in a discharge temperature from the electrochemical device that is optimized for a subsequent stage, for example, a condenser stage of a vapor compression cycle.

In some embodiments, the disclosed electrochemical devices can be employed as one or more components of a heating/cooling system, such as but not limited to a vapor compression cycle, or as one or more components of a power generation system, such as but not limited to an organic Rankine cycle (ORC) and a Brayton cycle. In any cycle in which the electrochemical device is employed, the fluid transported by the electrochemical device and/or the working fluid of the cycle can have HFO (or combination of HFOs) as the sole component or as one component out of multiple components (e.g., combined with a hydrofluorocarbon (HFC), such that the working fluid is an HFC/HFO mixture). Embodiments of the disclosed HFO-based heating/cooling systems can be used to provide heat pumping, refrigeration, cooling, or air-conditioning, while embodiments of the disclosed HFO-based power generation system can be used to provide electrical power.

Figure 1A:
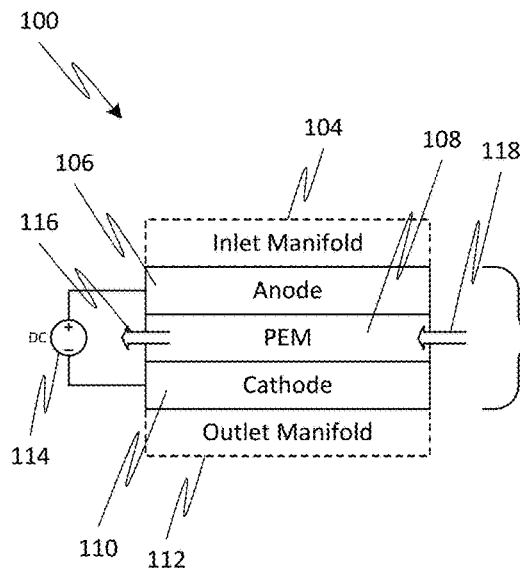
FIG. 1A is a simplified schematic diagram illustrating aspects of electrochemical processing of hydrofluoroolefins (HFO), according to one or more embodiments of the disclosed subject matter.
Figure 1A:
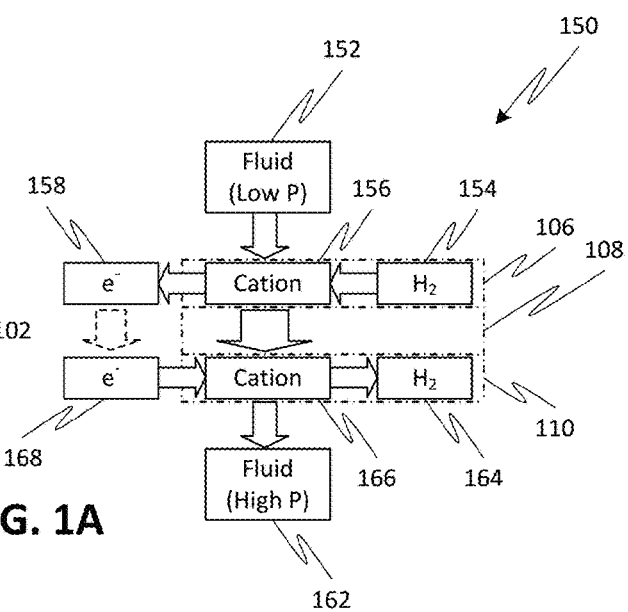

For example, FIG. 1A illustrates aspects of an electrochemical device 100 acting on HFO fluid. The electrochemical device 100 includes a proton exchange membrane (PEM) 108 disposed between a pair of gas-permeable electrodes 106, 110. The PEM 108 can include a membrane electrolyte, for example, an ionomer, such as but not limited to sulfonated tetrafluoroethylene-based fluoropolymer-copolymer (e.g., Nafion®), perfluorosulfonic acid (PFSA), polystyrene sulfonic acid (PSSA), and carboxymethyl cellulose (CMC). The electrodes 106, 110 are formed of or coated with an appropriate catalyst that facilitates reactions of the HFO fluid and/or carrier gas (e.g., hydrogen). For example, the electrodes 106, 110 can be formed of or coated with platinum (Pt), a metal hydride, or any other suitable material. The catalyst material of the anode electrode 106 can be the same as or different from the catalyst material of the cathode electrode 110.

The assembly of the electrodes 106, 110 to PEM 108 can be considered an integral membrane electrode assembly (MEA) 102 and can be separately coupled to inlet gas distribution manifold 104 (i.e., suction-side or feed-side volume) and outlet gas distribution manifold 112 (i.e., discharge-side volume) to convey fluid and/or carrier gas to/from the PEM 108. DC voltage source 114, connected to the electrodes 106, 110, applies an electric field to the PEM 108 to drive transport of the HFO fluid, in particular, the ionic form of the HFO, therethrough.

Figure 7A:
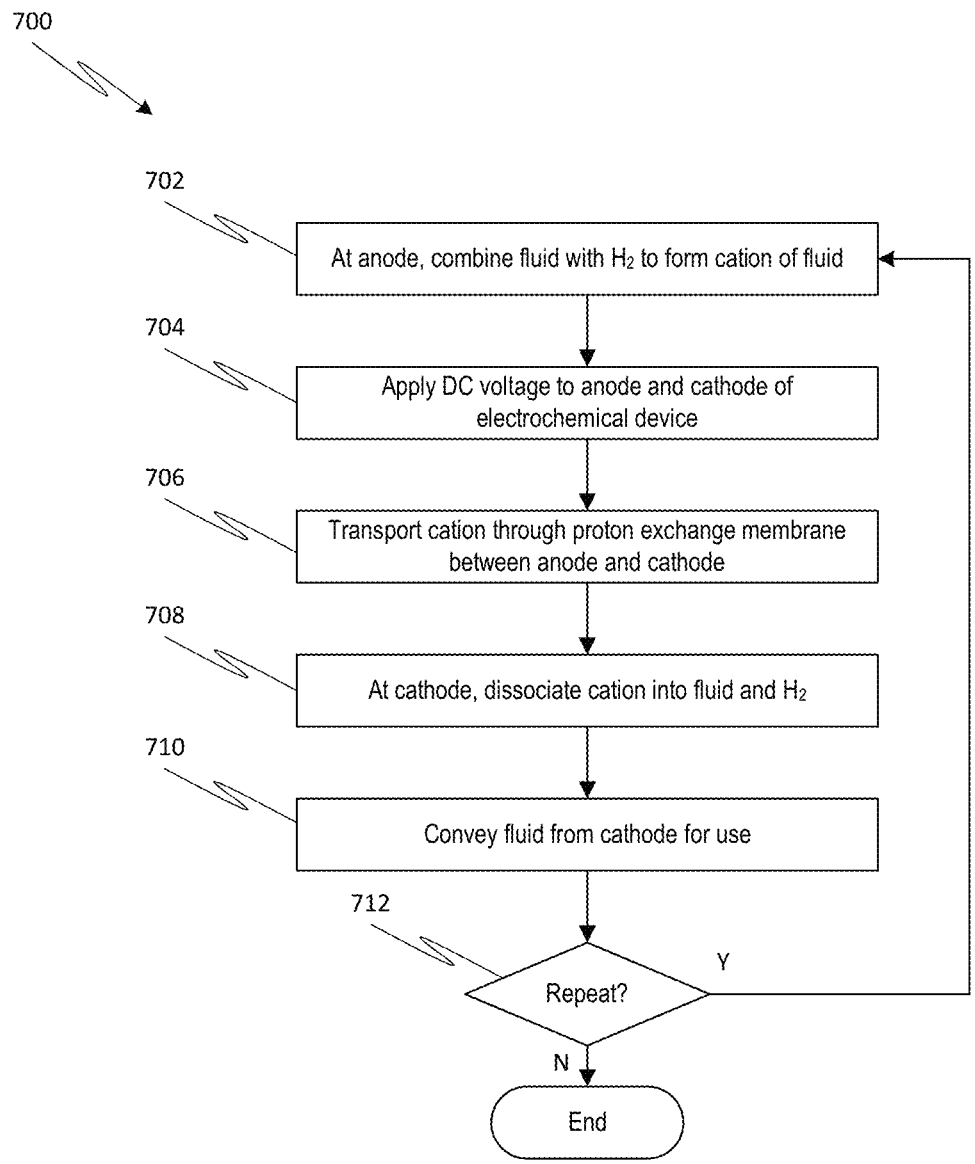
FIG. 7A is an exemplary process flow diagram for electrochemical compression of HFO, according to one or more embodiments of the disclosed subject matter.

Referring to FIG. 7A and the generalized electrochemistry 150 illustrated at right in FIG. 1A, the electrochemical process 700 using device 100 includes, at 702, combining HFO fluid 152 with hydrogen carrier gas 154 (i.e., $H_2$) to form a cation 156 of the HFO. The HFO 152 can be provided to the inlet manifold 104 of electrochemical device 100 from another process, for example, an evaporating heat exchanger of a vapor compression cycle. The $H_2$ carrier gas 154 can be part of the anode 106 (e.g., absorbed within a material of the electrode, as explained in further detail below) or externally supplied to the anode 106, for example, separate from the HFO (e.g., via a separate inlet to the inlet manifold 104) or as part of the fluid supplied to the inlet manifold (e.g., as a mixture of HFO and $H_2$).

At the anode 106, interaction with the catalyst causes a reaction between the HFO and $H_2$ carrier gas to form the HFO cation 156 and electrons 158. For example, when the HFO is R-1234yf (i.e., $CH_2CFCF_3$), the catalyst-facilitated reactions at the anode 106 to form the corresponding HFO cation $CH_3CFCF_3^+$ are given by:

$$H_2 \rightarrow 2H^+ + 2e^-$$

$$2H^+ + 2CH_2CFCF_3 \rightarrow 2CH_3CFCF_3^+ \quad (1)$$

In those embodiments where fluid is a mixture of HFO with other components (e.g., HFC), each component may form its own cation or may form a common cation with HFO for transport through the PEM.

The process 700 can proceed to 704, where voltage source 114 applies an electric field to the anode 106 and cathode 110 of the MEA 102, such that, at 706, the HFO cation 156 is transported from the anode 106 side through PEM 108 to the cathode 110 side. In the transport 706, the proton of the $H_2$ gas serves as a carrier for the HFO fluid. The HFO fluid in the ionic form (i.e., the cation 156) can move freely in the PEM 116 via an ion hopping mechanism. For example, the cation 156 can attach to sulfonic acid functional groups in PEM 116 and can readily hop from one sulfonic acid functional group to another sulfonic acid functional group, driven by the DC voltage potential supplied by power supply 114.

At the cathode 110, the catalyst facilitates dissociation of the transported HFO cation 166 in order to reform the constituent HFO and $H_2$ carrier gas at 708. In essence, 708 is the reverse process of 702, with electrons 168 (i.e., from voltage source 114) combining with the transported cation 166 to regenerate $H_2$ gas 164 and HFO 162. For example, when the HFO is R-1234yv, the catalyst-facilitated reactions at the cathode 110 are given by:

$$2CH_3CFCF_3^+ \rightarrow 2H^+ + 2CH_2CFCF_3$$

$$2H^+ + 2e^- \rightarrow H_2 \quad (2)$$

When the HFO fluid is in the vapor phase and if the external flow of HFO fluid from the discharge-side to the feed-side is regulated, the resulting HFO 162 at the discharge-side can be at a higher pressure than the HFO 152 at the inlet-side. When the HFO fluid is in the liquid phase, the resulting HFO 162 at the discharge-side can be at the same or higher pressure than the HFO 152 at the inlet-side.

The transported HFO 162 in outlet manifold 112 can then be conveyed for further processing and/or use at 710, for example, as input to a condensing heat exchanger, as input to a combustion chamber, or as input to an evaporating heat exchanger. At 712, it can be determined if the process 700 should be repeated, for example, as part of a heating/cooling or power generation cycle, in which case the process 700 returns to 702.

Although 702-712 are illustrated separately in FIG. 7A, it is contemplated that such process steps may occur contemporaneously, for example, during the continuous operation of a heating/cooling or power generation cycle. Moreover, the particular order of 702-712 in FIG. 7A has been chosen for explanatory purposes only and is not intended to be limiting. Indeed, in practical embodiments of the disclosed subject matter, the illustrated steps may occur before or during other steps. For example, the electric field application of 704 may occur before or during the forming the cation of 702.

Under constant application of the electric field (i.e., DC voltage), for example, as part of a heating/cooling or power generation cycle, the electrochemical process can be continuous. The resulting pressure of the transferred HFO may be a function of the applied electric field as well as the feed/discharge flow conditions. The pressure relationship may be given by the Nernst equation:

$$E = \frac{RT}{nF} \ln\left(\frac{P_d}{P_s}\right) \quad (3)$$

where $P_d$ represents the discharge pressure (i.e., at outlet manifold 112), $P_s$ represents the suction pressure (i.e., at inlet manifold 104), n represents the number of electrons 158 released by each $H_2$ molecule 154 transferred across PEM 108, and E represents the electrochemical cell voltage charge (i.e., supplied by power supply 114). Thus, the Nernst equation gives the ideal DC voltage needed to reach a desired partial pressure ratio. In practical embodiments, however, the total internal resistance of the electrochemical device 100, any contact resistance, and electrode polarization can result in parasitic losses that yield deviations from the ideal relationship defined by the above Nernst equation.

The ideal transfer rate of HFO fluid through the PEM can be calculated based on Faraday's law:

$$\frac{dn}{dt} = \frac{I}{nF} \quad (4)$$

where I is the current flowing through the external circuit (i.e., power supply 114), n is the number of electrons 158 transferred in the cation 156 formation, and F is the Faraday's constant. However, actual flow rates in physical embodiments may deviate slightly from the ideal predicted flow rate, for example, due to $H_2$ or HFO crossover phenomena.

PEM 108 may require supplemental water (i.e., humidity) for efficient ionic conduction of the cation therethrough for an appropriate HFO transfer rate. Thus, in some embodiments, the electrochemical compressor 100 can have a water or humidity input 118. For example, humidity input 118 may be achieved by humidifying the input fluid prior to or at inlet manifold 104 (e.g., by a suction line humidifier). Other options for providing water 118 to PEM 108 are also possible according to one or more contemplated embodiments.

As referenced above, in some embodiments, $H_2$ carrier gas may be provided to the inlet manifold 104 separately from the HFO fluid or as part of the fluid (i.e., HFO+$H_2$ mixture) circulating in the system. However, the circulating $H_2$ gas may represent a safety issue and undermine the efficiency of the system. Thus, in some embodiments, the electrochemical device 100 can be constructed to restrict $H_2$ from circulating outside of the MEA 102. For example, the anode 106 and the cathode 110 can include a hydrogen-absorbing material, such as metal hydride. At the anode 106, the hydrogen-absorbing material can store $H_2$ therein and can release as $H_2$ gas 154 for combination with the HFO 152. Similarly, at the cathode 110, the hydrogen-absorbing material can receive $H_2$ gas 164 from the dissociation of cation 166 and store the $H_2$ therein. As a result, the $H_2$ gas only migrates within the MEA 102. Once the hydrogen-absorbing electrodes have been expended (i.e., when the anode 106 has released all of its stored $H_2$ or when the cathode 110 has reached its capacity for storing $H_2$), the electrodes can be regenerated, such as by reversing the flow through the electrochemical device 100, for example, as described below with respect to FIGS. 6A-6G.

The electrochemical process 150 uses energy input in the form of a voltage charge supplied, for example, by power supply 114. As a result, the electrochemical device 100 may be heated, which in turn may increase a temperature of the discharged HFO 162. This increased temperature of the discharged HFO 162 can eventually degrade performance (i.e., by increasing a temperature of the HFO 152 at the feed side) and may increase energy consumption of the device 100. As compared to conventional mechanical compressors, the electrochemical device 100 has relatively large surface areas (e.g., of PEM 108) for passive cooling.

Alternatively or additionally, heat 116 can be removed from the MEA 102 and/or the discharge HFO 162 via active cooling to yield a substantially temperature-controlled compression process 150. For example, heat 116 can be removed by heat exchangers thermally coupled to the outlet manifold 112. Such a heat exchanger can be an open channel heat exchanger (e.g., where a cooling air is flowed through a channel in or adjacent to channels in the outlet manifold 112), a microchannel flat tube array thermally coupled to the outlet manifold 212 and/or the MEA 102 (e.g., which can use higher density fluid than air), a metal foam heat exchanger thermally coupled to the outlet manifold 212 and/or the MEA 102, or any other type of heat exchanger setup. In some embodiments, the active cooling can yield a temperature for the HFO discharge 162 that has been chosen to maximize system performance (or to at least improve performance of a heating/cooling or power generation system, such as a vapor compression system). For example, the HFO discharge may have a temperature value slightly higher than that of the condenser of a vapor compression system.

When operated in an expansion mode, the electrochemical device transports cations of the HFO fluid through the proton exchange membrane to generate an electric field, such that a pressure of the HFO fluid on an outlet side of the membrane is lower than on an inlet side. The generated electric field can be used to recapture power expended by other components of the heating/cooling or power generation cycle (e.g., the power required to operate an electrochemical device in the compression/pumping mode). Thus, the electrochemical device operating in the expansion mode may be considered a power harvesting device.

Figure 1B:
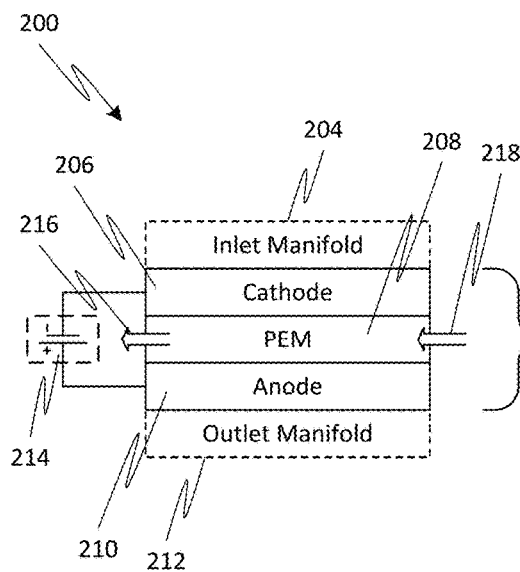
FIG. 1B is a simplified schematic diagram illustrating aspects of another electrochemical processing of HFO, according to one or more embodiments of the disclosed subject matter.
Figure 1B:
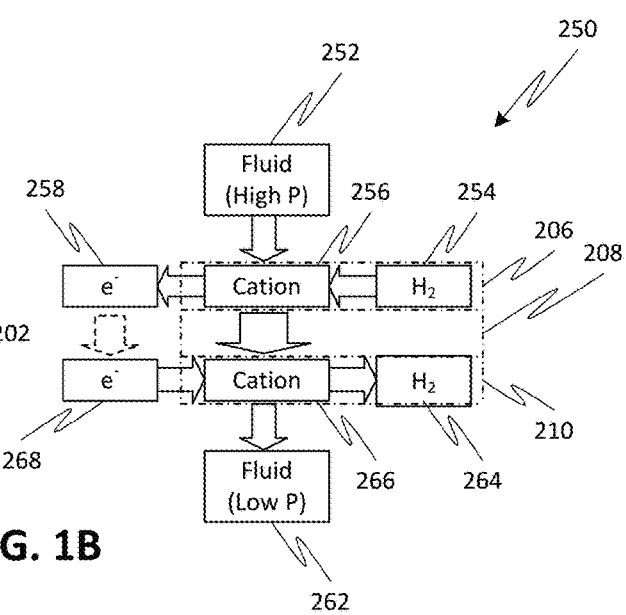

In effect, the expansion mode operation is the reverse process of the compression/pumping mode operation described above with respect to FIGS. 1A and 7A. For example, FIG. 1B illustrates aspects of an electrochemical expander 200 acting on HFO fluid. As with the electrochemical compressor 100, the electrochemical expander 200 has PEM 208 disposed between a pair of gas-permeable electrodes 206, 210 operating as cathode and anode, respectively. The assembly of the electrodes 206, 210 to PEM 208 can be considered an integral membrane electrode assembly (MEA) 202 and can be separately coupled to inlet gas distribution manifold 204 and outlet gas distribution manifold 212 to convey fluid and/or carrier gas to/from the PEM 208. However, in contrast to the electrochemical device 100 setup, the electrochemical expander 200 has an opposite polarity (i.e., cathode 206 on inlet side and anode 210 on outlet side). An electric field can be generated between the electrodes 206, 210 by passing the ionic form of the HFO fluid through the PEM 208, which electric field can be captured by the system for use in powering other components (e.g., for use by or to supplement power supply 114) or stored by an optional power storage device 214 (e.g., battery) for later use.

In some embodiments, the electrochemical expander 200 may be the same device as electrochemical device 100 but operating in a reverse flow direction with opposite polarity.

Thus, heat 216 can be removed and/or humidity 218 added in a manner similar to that described above for electrochemical device 100. Moreover, electrodes 206, 210 may be constructed to retain $H_2$ carrier gas within MEA 202 in a manner similar to that described above for electrochemical device 100.

Figure 7B:
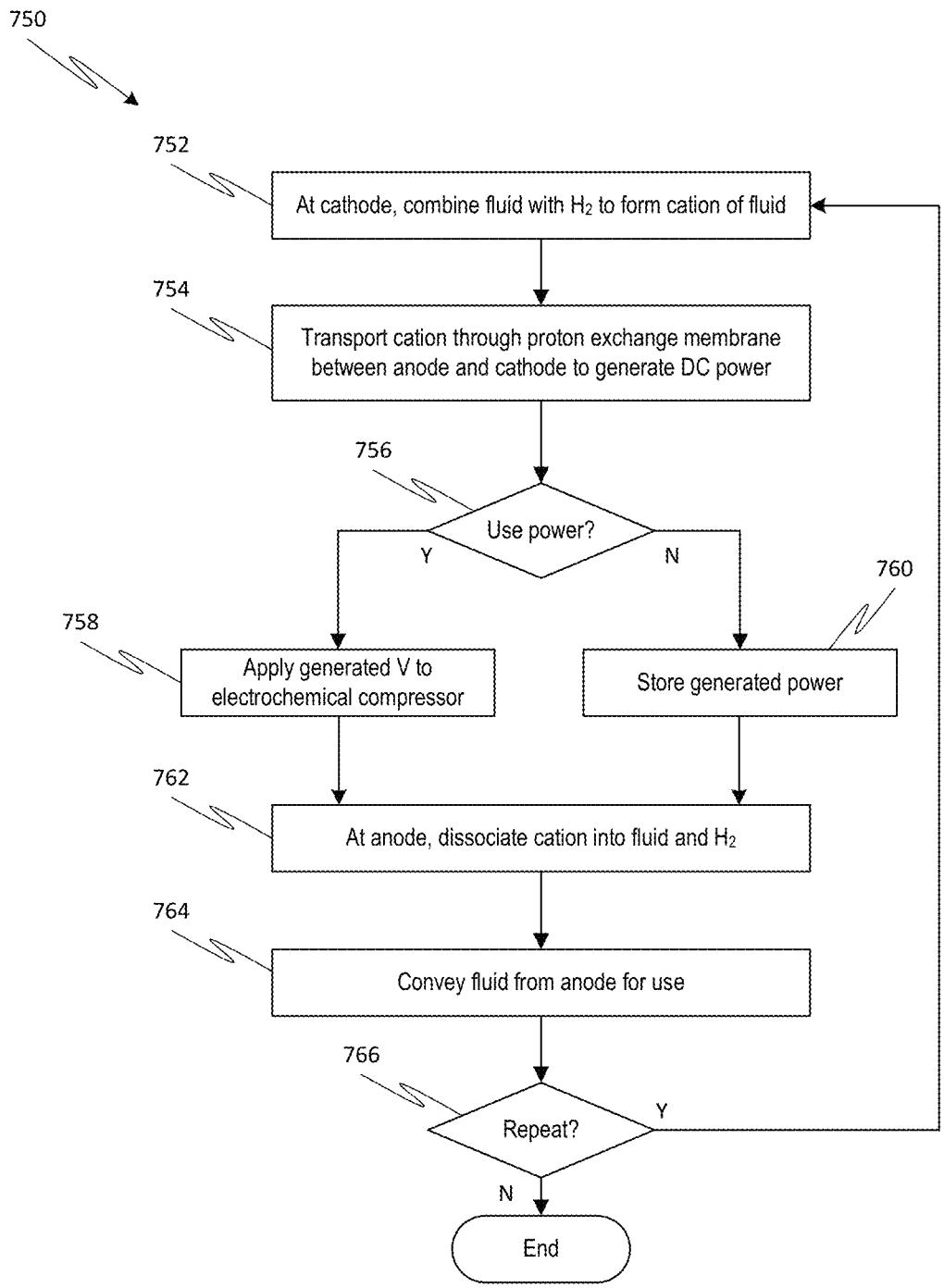
FIG. 7B is an exemplary process flow diagram for electrochemical expansion of HFO, according to one or more embodiments of the disclosed subject matter.

Referring to FIG. 7B and the generalized electrochemistry 250 illustrated at right in FIG. 1B, the electrochemical expansion process 750 using device 200 includes, at 752, combining HFO fluid 252 at a relatively high pressure (which may be the same as or different from the pressure of HFO 162 at outlet manifold 112 of electrochemical compressor 100 in a heating/cooling or power generation cycle) with $H_2$ carrier gas 254 to form a cation 256 of the HFO. The high-pressure HFO 252 can be provided to inlet manifold 204 of electrochemical expander 200 from another process of the heating/cooling or power generation cycle, e.g., a condensing heat exchanger, an evaporating heat exchanger, or a combustion chamber. As with the compression process 700, the $H_2$ carrier gas 254 can be part of the cathode 206 (e.g., absorbed within a material of the electrode, as explained in further detail below) or externally supplied to the cathode 206, for example, separate from the HFO (e.g., via a separate inlet to the inlet manifold 204) or as part of the fluid supplied to the inlet manifold (e.g., as a mixture of HFO and $H_2$).

At the cathode 206, interaction with the catalyst causes a reaction between the HFO and $H_2$ carrier gas to form the HFO cation 256 and electrons 258. The process 750 can proceed to 754, where the HFO cation 256 is transported from the cathode 206 side through PEM 208 to the anode 210 side, for example, by a pressure gradient across the PEM 208. The transport of HFO cation 256 can generate an electric field (i.e., DC power). At 756, it is determined whether the generated power is to be used at 758 (e.g., to power another component of the system, such as the electrochemical compressor 100) or to be stored at 760 (e.g., by charging a battery).

At the anode 210, the catalyst facilitates dissociation of the transported HFO cation 266 to reform the constituent HFO and $H_2$ carrier gas at 762. In essence, 762 is the reverse process of 752, with electrons 268 combining with cation 266 to regenerate the H$_2$ gas 264 and HFO 262. If the external flow of HFO fluid from the discharge-side to the feed-side is regulated, the resulting HFO 262 at the discharge-side can be at a lower pressure. The resulting low pressure HFO 262 in outlet manifold 212 (which pressure may be the same as or different from the pressure of HFO 152 at inlet manifold 104 of electrochemical device 100 in the heating/cooling or power generation cycle) can then be conveyed for further processing and/or use at 764, for example, as the input to an evaporating heat exchanger or the input to a condensing heat exchanger. Alternatively or additionally, the HFO 262 from outlet manifold 212 can be exhausted as waste at 764. At 766, it can be determined if the process 750 should be repeated, for example, as part of a heating/cooling or power generation cycle, in which case the process 750 returns to 752.

Although 752-766 are illustrated separately in FIG. 7B, it is contemplated that such process steps may occur contemporaneously, for example, during the continuous operation of a heating/cooling or power generation cycle. Moreover, the particular order of 752-766 in FIG. 7B has been chosen for explanatory purposes only and is not intended to be limiting. Indeed, in practical embodiments of the disclosed subject matter, the illustrated steps may occur before or during other steps.

Thus, an electrochemical device can be constructed for HFO compression/pumping or for HFO expansion (and potential power recovery). In some embodiments, the electrochemical device can be constructed to be switchable between an HFO compression/pumping mode (where the MEA has a first polarity and HFO flow is in a first direction) and an HFO expansion mode (where the MEA has a second polarity opposite the first, and HFO flow is in a second direction opposite the first). Regardless of the operational configuration, the electrochemical device may have a similar device construction.

Figure 2A:
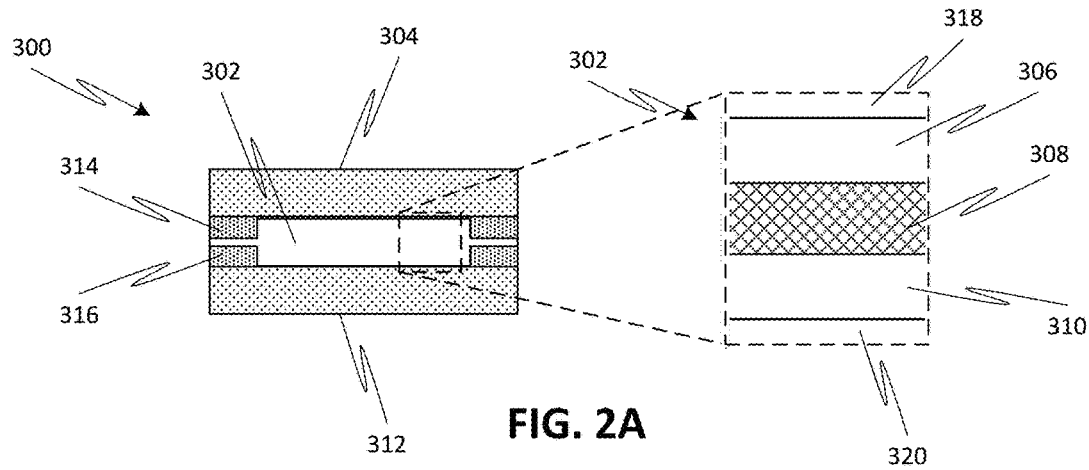
FIG. 2A is a simplified cross-sectional view of an electrochemical device, according to one or more embodiments of the disclosed subject matter.

For example, FIGS. 2A-2B illustrate an exemplary device construction for an electrochemical device cell 300 (or unit). The electrochemical cell 300 can include a membrane electrode assembly 302, which comprises PEM 308 between a pair of gas-permeable electrodes 306, 310. An end plate 304 with one or more channels 318 therein can serve as a first gas distribution manifold (inlet or outlet manifold depending on operation of cell 300). Layout and/or geometry of channel(s) 318 can be substantially the same or differ across end plate 304. An inlet/outlet face of end plate 304 can face electrode 306 such that channel(s) 318 are in fluid communication with MEA 302. A sealing gasket 314 can be disposed between the end plate 304 and the MEA 302 to prevent leakage of HFO and/or H$_2$ from within device 300.

An opposing end plate 312 with one or more channels 320 therein can serve as a second gas distribution manifold (inlet or outlet manifold depending on operation of cell 300). Layout and/or geometry of channel(s) 320 can be substantially the same or differ across end plate 312. Moreover, layout and/or geometry of channel(s) 320 of end plate 312 can be substantially the same as the layout and/or geometry of channel(s) 318 of end plate 304, for example, when device 300 is constructed to reverse HFO flow to switch between compression and expansion modes. Alternatively, layout and/or geometry of channel(s) 320 of end plate 312 can differ from the layout and/or geometry of channel(s) 318 of end plate 304. An inlet/outlet face of end plate 312 can face electrode 310 such that channel(s) 320 are in fluid communication with MEA 302. A sealing gasket 316 can be disposed between end plate 312 and MEA 302 to prevent leakage of HFO and/or H$_2$ from within device 300.

The inlet/outlet face of end plate 304 may also be in electrical contact with electrode 306. Similarly, the inlet/outlet face of end plate 312 may be in electrical contact with electrode 310. Thus, the electric field can be applied to electrodes 306, 310 (and thus PEM 308) via end plates 304, 312, respectively. Alternatively, respective electrical connections may be routed through end plates 306, 312, through gaskets 314, 316, or through a portion of MEA 302 so as to apply the electric field to respective electrodes 306, 310 without directly energizing manifolds 304, 312.

The gas distribution manifolds 304, 312 may be formed of a material substantially resistant to degradation to electricity and/or the chemistry present during operation of electrochemical device 300. Moreover, the manifolds 304, 312 may be constructed to resist the fluid pressures generated during operation and/or to conduct electricity and/or heat. For example, the manifolds 304, 312 may be constructed of graphite or stainless steel, although other materials are also possible according to one or more contemplated embodiments.

Within each gas distribution manifold, the channel layout and/or geometry can be designed to account for pressure and fluid flow variations. For example, FIG. 3A shows a perspective view of the outlet face of an inlet manifold 350 for an electrochemical compressor. The manifold 350 has a serpentine channel 354 that can be used to ensure the HFO fluid flows in only one direction from inlet 352, thereby enabling better distribution on the surface of the MEA. The width of the channel 354 can increase as it gets closer to the suction link 352 (inlet) in order to accommodate the flow change and pressure drop. Thus, channel cross-section at 358, which is farther from inlet 352, is reduced as compared channel cross-section 356, which is closer to inlet 352.

FIG. 3B shows a cross-sectional view 350a of the portions 356, 358 of FIG. 3A, where a width W$_2$ (i.e., at face 360 adjacent the MEA) of channel cross-section 358a is less than a width W$_1$ of channel cross-section 356a. However, it is also possible for the height of the channel 354 (i.e., from face 360 adjacent the MEA to a bottom of the channel 354) to be changed instead of the width. For example, FIG. 3C shows a cross-sectional view 350b of a variation where channel cross-section 358b has a width W$_1$ that is the same as that of channel cross-section 356b but has a height H$_2$ that is less than a height H$_1$ of channel cross-section 356b. However, it is also possible for both the height and the width of the channel 354 to be changed, for example, as illustrated by cross-sections 356c, 358c in the cross-sectional view 350c of FIG. 3D. Thus, the channel geometry can be designed to account for pressure and fluid flow variations, by changing a cross-sectional dimension (i.e., width, height, or width and height) of the channel based on its location with respect to an inlet or outlet of the manifold.

Similarly, FIG. 3E shows a perspective view of the inlet face of an outlet manifold 370 for an electrochemical device. Because the outlet manifold 370 receives higher pressure fluid, the manifold 370 can include an array 380 of substantially similar parallel channels to accommodate the higher pressure and flow distribution. A collection channel 374 can be disposed at one end of array 380 to collect the discharged fluid and to direct it to a single outlet 372. The cross-sectional area of the collection channel 374 (e.g., the width, height, or combination of width and height) can increase as it gets closer to the discharge link 372 (outlet) in order to accommodate the increased mass flow and pressure drop. Thus, channel cross-section at 378, which is farther from outlet 372, is reduced as compared channel cross-section 376, which is closer to outlet 372. An optional constant-cross-section collection channel 382 can be disposed at an end of array 380 opposite the outlet 372 to allow fluid communication between channels in array 380. Alternatively, the end of array 380 opposite outlet 372 may be closed off, such that working fluid collected in the channels of the array can only exit the respective channel at the end connecting to collection channel 374.

The discussion above has focused on a single electrochemical cell. However, the flow rate of HFO fluid through a single electrochemical cell may be insufficient for practical embodiments. Thus, in some embodiments, multiple electrochemical unit cells (whether pump/compressor, expander, or switchable compressor/expander) can be coupled together (serially or in parallel) to form an electrochemical device stack. In this way, the HFO flow rate can be increased and/or the desired pressure lift across the electrochemical device can be achieved.

Figure 4A:
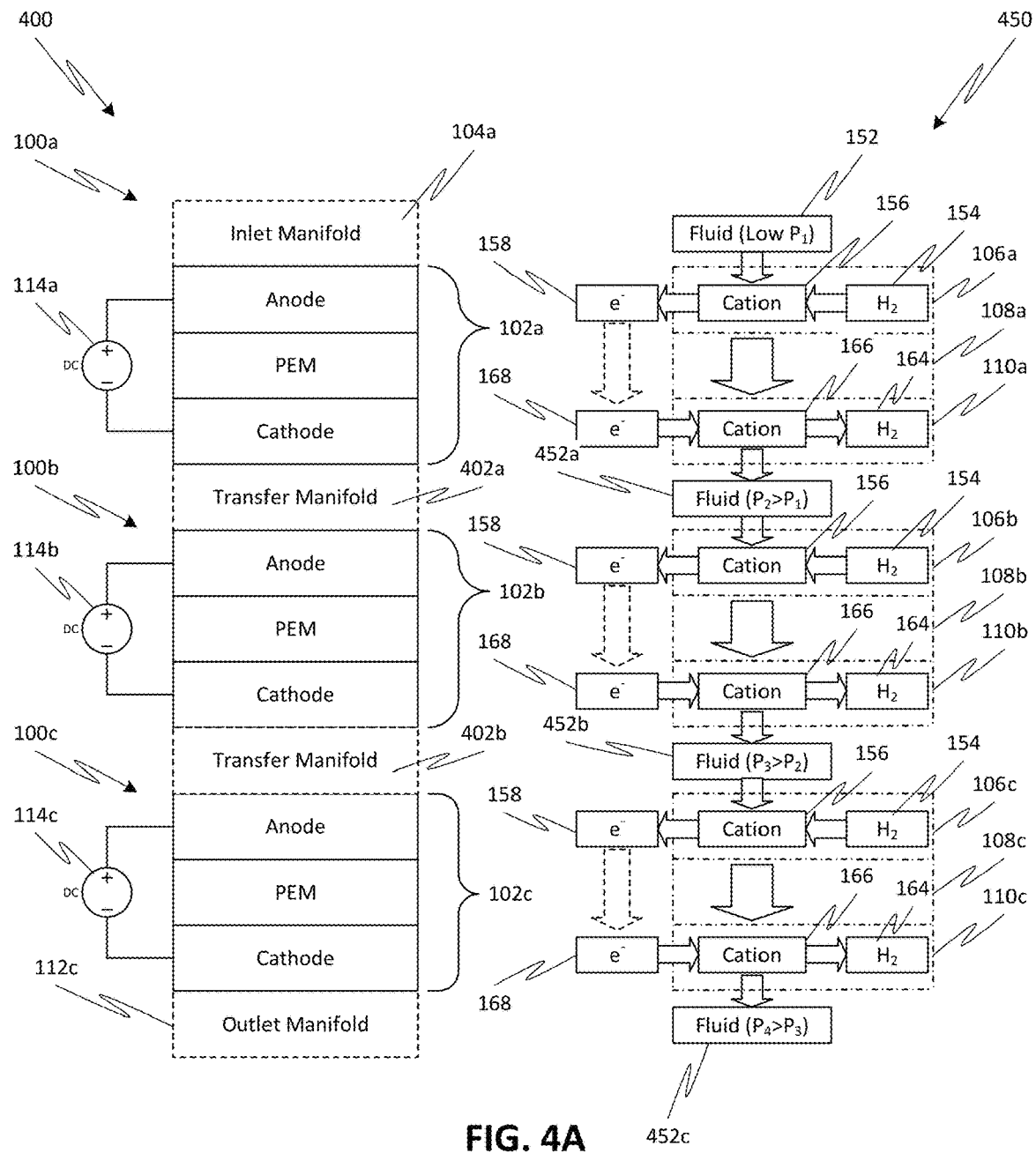
FIG. 4A is a simplified schematic diagram illustrating aspects of electrochemical processing with serially stacked devices, according to one or more embodiments of the disclosed subject matter.

For example, FIG. 4A illustrates a configuration (and corresponding electrochemical process 450) of electrochemical unit cells 100a-100c coupled together in series to form an electrochemical stack 400. The HFO fluid 152 at a relatively low pressure $P_1$ enters the stack 400 via inlet manifold 104a. In a first stage configured by unit cell 100a, the HFO fluid 152 is driven through the MEA 102a by electric field applied by power supply 114a, as described above with respect to FIG. 1A, to yield fluid 452a at a pressure $P_2$ higher than $P_1$. The fluid 452a is transferred from the first stage to a second stage, configured by unit cell 100b, by a transfer manifold 402a. In the second stage, the HFO fluid 452a is transported through MEA 102b by electric field applied by power supply 114b, as described above with respect to FIG. 1A, to yield fluid 452b at a pressure $P_3$ higher than $P_2$. The process repeats for a third stage, configured by unit cell 100c, to yield working fluid 452c at a final pressure $P_4$ higher than $P_3$. Of course, although three serial stages 100a-100c are illustrated in FIG. 4A, additional or fewer serial stages are also possible according to one or more contemplated embodiments.

For example, each transfer manifold 402a, 402b can be a combination of an outlet manifold (e.g., end plate 370 in FIG. 3E) and an inlet manifold (e.g., end plate 350 in FIG. 3A) where the outlet port 372 of the outlet manifold is coupled to the inlet port 352 of the inlet manifold. Alternatively, each transfer manifold 402a, 402b can include a channel geometry that directly conveys the HFO fluid from one MEA 102 to the next MEA 102 in the sequence. However, after each unit cell 100 stage, the density of the transported fluid increases along with the pressure. Thus, the respective channel size (i.e., cross-sectional geometry) of the transfer manifold 402 may decrease with each subsequent stage, such that transfer manifold 402b has a smaller channel cross-section and/or total volume as compared to transfer manifold 402a.

As noted above, the power consumed in the electrochemical device can generate a considerable amount of heat, which may affect performance of the system. Thus, in embodiments, the generated heat may be removed, for example, by including cooling elements in the transfer manifolds 402a-402b and/or outlet manifold 112c. For example, when the transfer manifold 402a, 402b is configured as a combination of outlet manifold and inlet manifold, an array of cooling channels (e.g., in a thermally conductive plate) may be disposed between the adjacent manifolds (i.e., sandwiched between the outlet and inlet end plates in a stack) to carry away heat by flowing a fluid therethrough. Alternatively or additionally, thermal management techniques similar to those applied for cooling of ion exchange membranes in hydrogen fuel cells may be applied to regulate a temperature of the disclosed electrochemical devices.

Figure 4B:
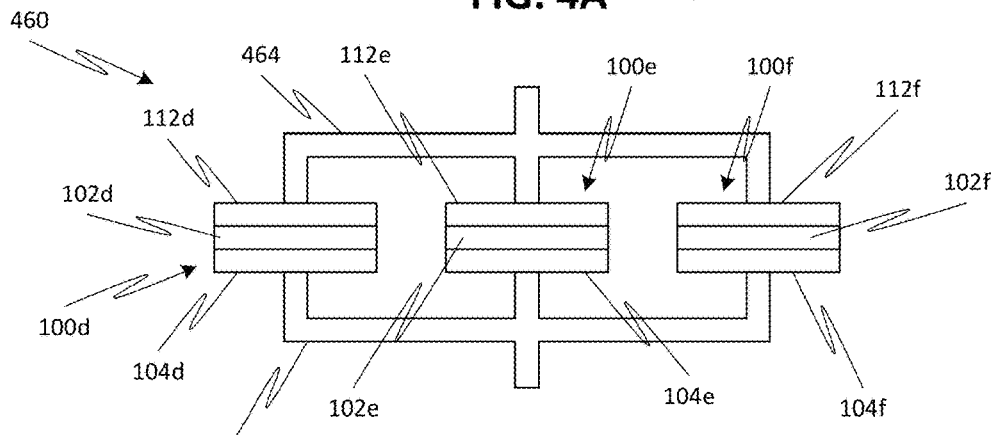
FIG. 4B is a simplified schematic diagram illustrating aspects of electrochemical processing with parallel stacked devices, according to one or more embodiments of the disclosed subject matter.

FIG. 4B illustrates an exemplary configuration of electrochemical unit cells 100d-100f coupled together in parallel to form an electrochemical stack 460. An inlet conduit 462 can direct HFO fluid at the suction side (i.e., at a relatively low pressure) in parallel to the respective inlet manifold 104d-104f of each unit cell 100d-100f. The unit cells 100d-100f can operate in parallel to pass HFO fluid through their respective MEAs 102d-102f to their respective outlet manifold 112d-112f, for example, as described above with respect to FIG. 1A. The resulting higher pressure HFO fluid can be collected from each unit cell 100d-100f by an outlet conduit 464, thereby producing a greater HFO flow rate than would otherwise be possible using only a single unit cell.

Of course, although three parallel stages 100d-100f are illustrated in FIG. 4B, additional or fewer parallel stages are also possible according to one or more contemplated embodiments. Moreover, although the serial configuration of FIG. 4A has been illustrated separately from the parallel configuration of FIG. 4B, it is also possible that the configurations may be combined. For example, each of the unit cells 100d-100f in FIG. 4B can be formed of the stack of serial unit cells 100a-100c in FIG. 4A (i.e., forming a 3×3 configuration of unit cells).

Figure 5A:
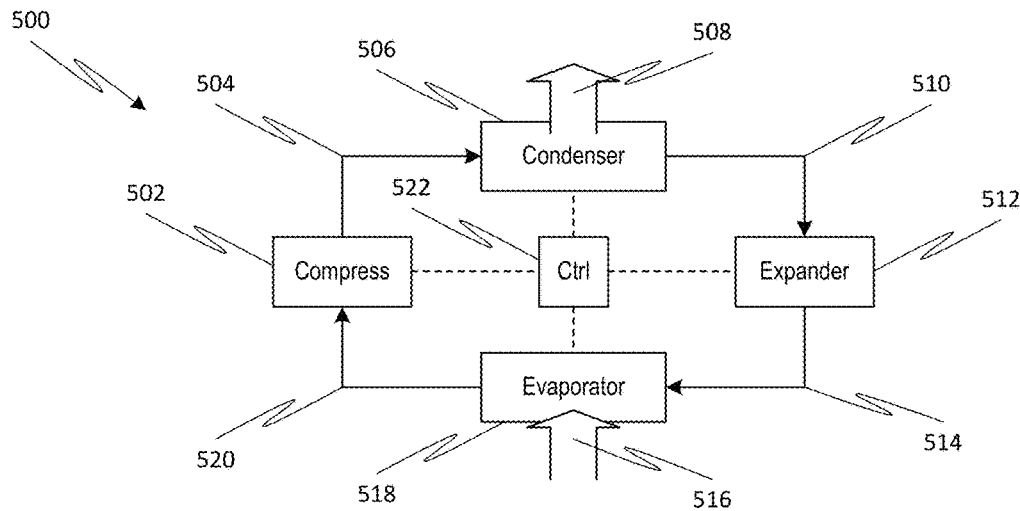
FIG. 5A is a simplified schematic diagram of a vapor compression system where an electrochemical device can be employed as one or more components, according to one or more embodiments of the disclosed subject matter.

As noted above, embodiments of the disclosed electrochemical device can be employed in a heating/cooling system, such as a vapor compression system, with HFO as a working fluid (i.e., refrigerant). For example, FIG. 5A illustrates an exemplary configuration of a vapor compression system 500, which may have a substantially conventional configuration other than the use of the electrochemical device(s) and HFO as refrigerant. For example, the vapor compression system 500 can have a heat exchanger 506 operating as a condenser, which transfers heat 508 from the working fluid circulating therethrough, and a heat exchanger 518 operating as an evaporator, which transfer heat 516 to the working fluid circulating therethrough. A controller 522 can be operatively coupled to the different components of the vapor compression system 500 to control operation and performance of the system, for example, to achieve a desired conditioned air temperature via exchange of heat 508 and/or 516.

In vapor compression system 500, the compressor 502 receives input HFO at 520. Generally, the HFO input 520 is in a vapor phase (e.g., saturated vapor); however, in some embodiments (e.g., under off-design conditions), the input HFO 520 may have both liquid and vapor phases (e.g., a high-quality two-phase state). In either case, the compressor 502 can compress the HFO input 520 to generate a higher pressure HFO at 504. The HFO at 504 may be superheated vapor. As noted above, heat may be removed from compressor 502 (i.e., from the discharged HFO) such that the temperature of discharged HFO is controlled for optimal performance of the vapor compression system 500 (e.g., to have a temperature at or slightly above that of the condenser 506). Heat 508 is transferred from HFO vapor 504 via heat exchanger 506 to condense the HFO. After condenser 506, the HFO at 510 may be saturated liquid. The expander 512 may receive the saturated HFO liquid 510 and further reduce a pressure thereof to generate a lower pressure HFO at 514, which may be a liquid-vapor HFO blend. Heat 516 is transferred to lower pressure HFO 514 via heat exchanger 518 to evaporate the HFO. The resulting saturated HFO vapor 520 (or high quality two-phase, as noted above) can be conveyed back to compressor 502, where the cycle can repeat.

Figure 5B:
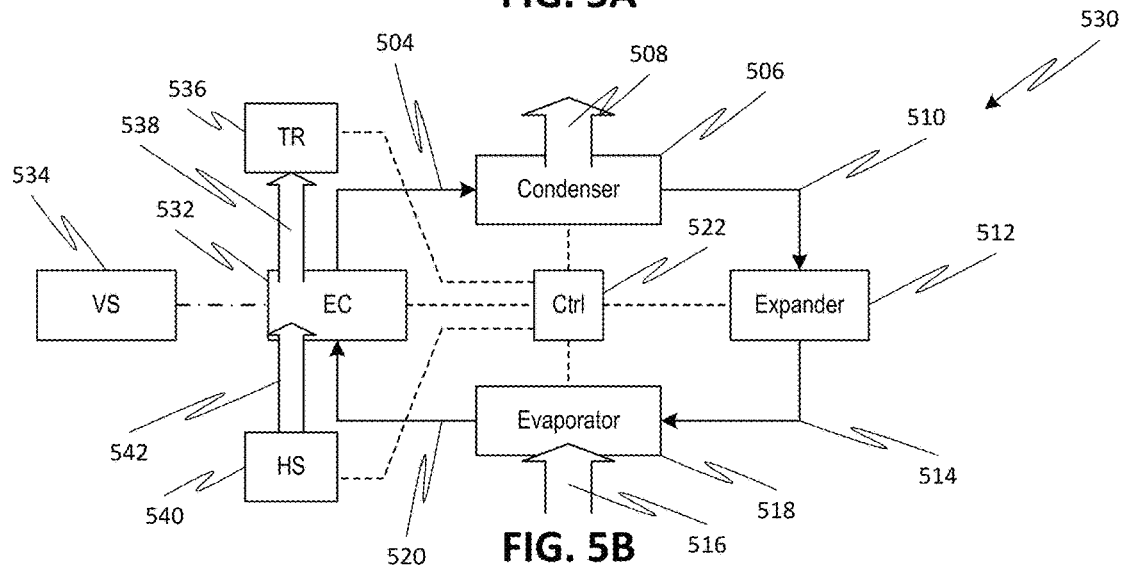
FIG. 5B illustrates an exemplary configuration of the system of FIG. 5A where an electrochemical device is used as a compressor, according to one or more embodiments of the disclosed subject matter.

The electrochemical device may be employed as compressor 502 and/or expander 512 in vapor compression system 500. For example, FIG. 5B shows a vapor compression system 530 where an electrochemical device 532 operates as compressor in a vapor compression cycle. The electrochemical device 532 may be similar to the compressor illustrated in FIG. 1A and described above, while the expander 512 may be a conventional device, such as an expansion or throttle valve. A voltage source 534 can be used to apply the electric field between electrodes of the MEA of the electrochemical compressor 532, thereby transporting the HFO working fluid through the PEM of the compressor 532. A thermal regulation unit 536 can transfer heat 538 from the electrochemical compressor 532 and/or the HFO working fluid discharged from the compressor 532 to yield a substantially optimal temperature of the HFO working fluid for use by system 530. A humidity/water source 540 can be used to transfer water 542 (i.e., water vapor) to the PEM of the compressor 532 (e.g., via direct provision to the PEM or by humidifying the HFO input to the compressor 532) to ensure efficient ion transfer.

Figure 5C:
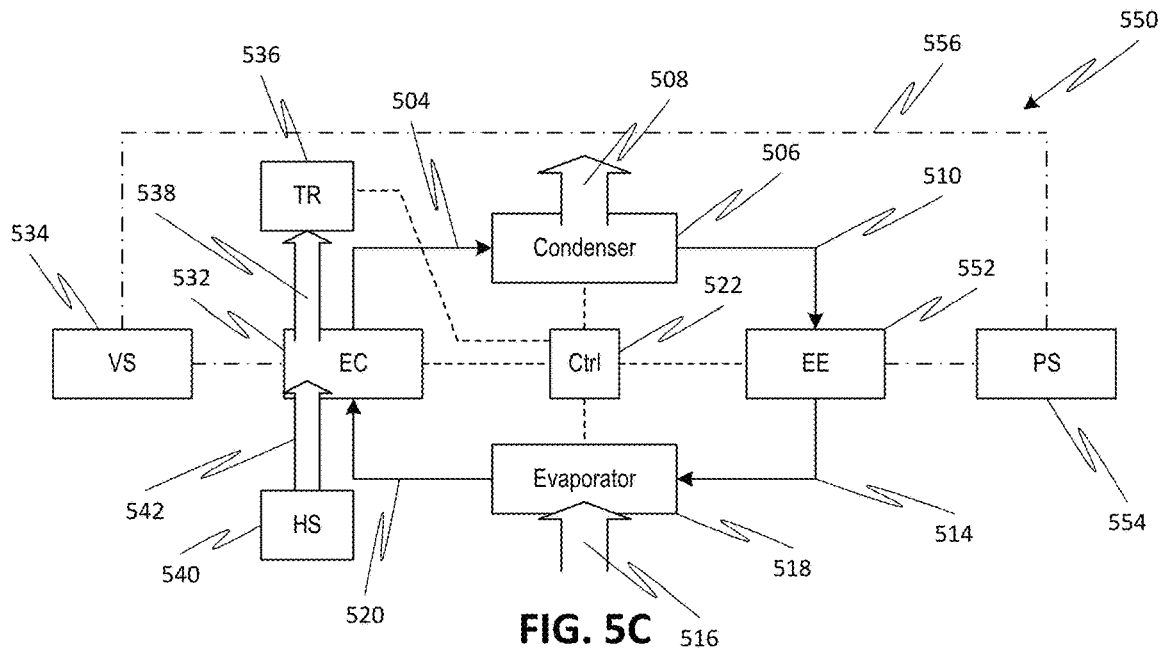
FIG. 5C illustrates another exemplary configuration of the system of FIG. 5A where electrochemical devices are used as compressor and expander, respectively, according to one or more embodiments of the disclosed subject matter.

Alternatively or additionally, the expander 512 of FIG. 5B can be replaced with an electrochemical device 552, for example, as shown in vapor compression system 550 of FIG. 5C. For example, the electrochemical device 552 may be similar to the expander illustrated in FIG. 1B and described above. Thus, as the HFO working fluid passes through the MEA of the electrochemical expander 552, electrical power may be harvested and used for powering different components of vapor compression system 550. For example, the harvested electrical power can power (at least in part) voltage source 534 of the electrochemical compressor 532 via power line 556. Alternatively or additionally, all or some of the harvested electrical power can be stored, for example, by charging power storage device 554 (e.g., battery).

Figure 5D:
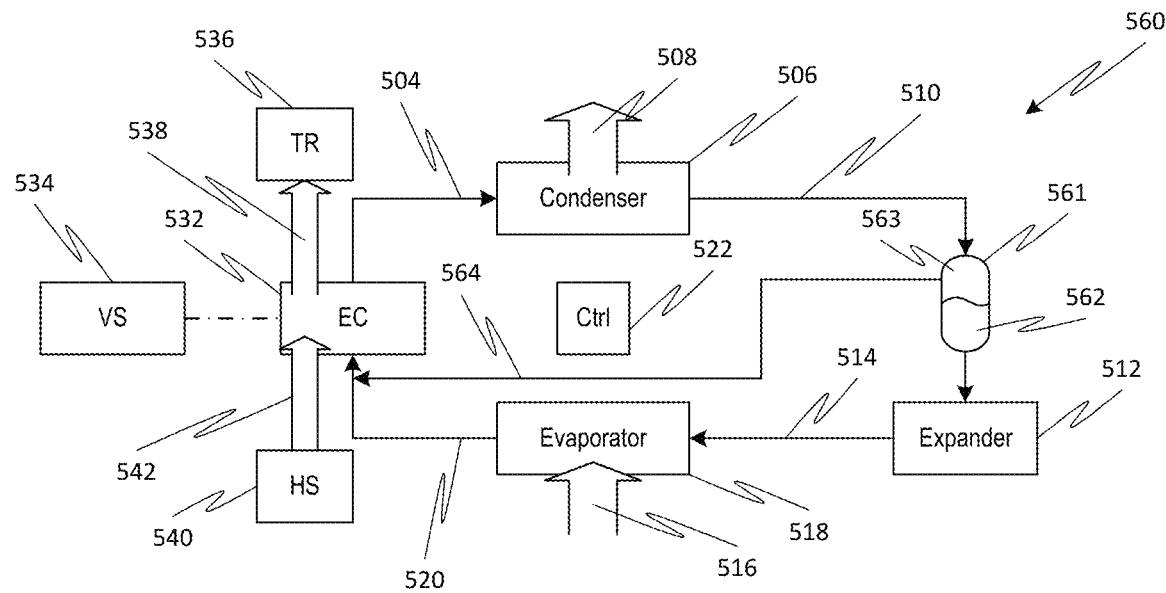
FIG. 5D illustrates another exemplary configuration of the system of FIG. 5A where an electrochemical device is used as a compressor with a phase separator for carrier gas recovery, according to one or more embodiments of the disclosed subject matter.

As noted above, the circulation of carrier gas in the heating/cooling system may impact efficiency of the system, for example, by undermining heat exchanger performance. Thus, in embodiments, the transport of the carrier gas through the system may be limited by one more capture components. For example, FIG. 5D illustrates an exemplary configuration of a vapor compression system 560, where a phase separator 561 is used to capture carrier gas. In particular, the phase separator 561 is disposed in the flow path between the condenser 506 and expander 512 and receives the saturated HFO output 510 from condenser 506. The system 560 can be configured such that, at a temperature and pressure in the phase separator 561, the carrier gas is in the vapor phase while the HFO is in the liquid phase. Any carrier gas thus separates from the liquid phase 562 of the HFO and coalesces at 563. The coalesced carrier gas 563 can be siphoned from the phase separator 561 and directed via input line 564 for reuse by the electrochemical compressor 532. Meanwhile, the substantially-carrier-gas-free HFO 562 can be output from the phase separator 561 to expander 512.

Figure 5E:
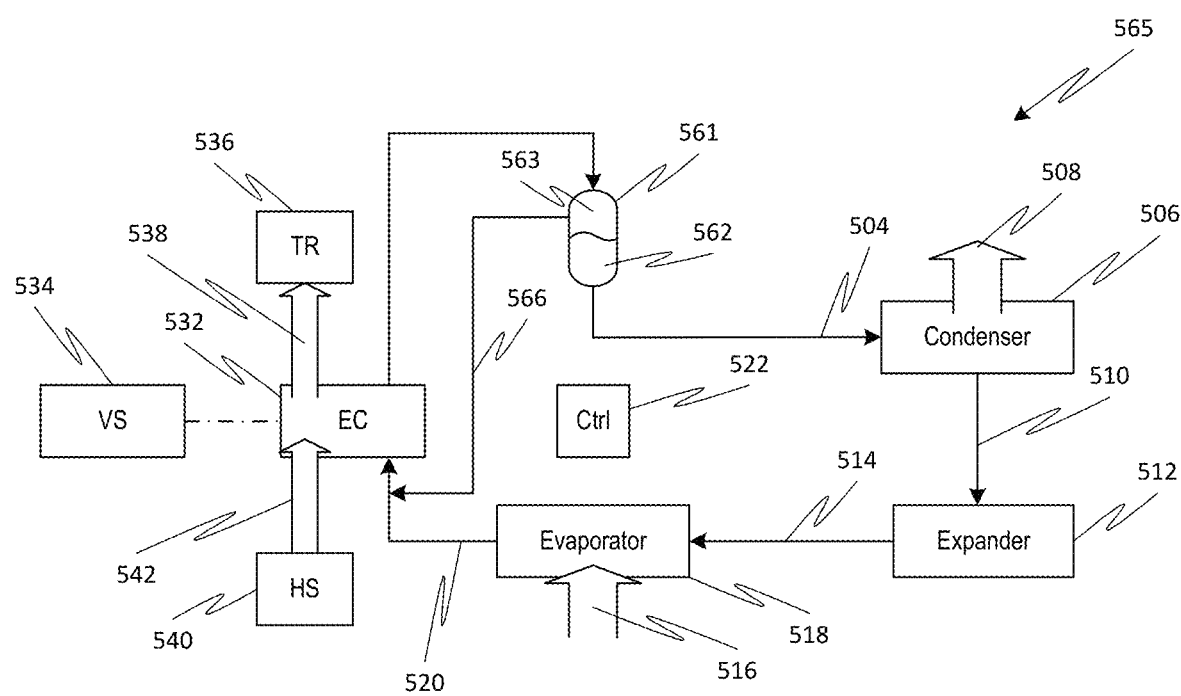
FIG. 5E illustrates a variation on of the configuration of FIG. 5D, where a phase separator is used for carrier gas recovery, according to one or more embodiments of the disclosed subject matter.

It is also possible to dispose the phase separator 561 at locations within the flow path of the vapor compression cycle different from that illustrated in FIG. 5D in order to capture and reuse the carrier gas exiting the electrochemical device 532. For example, FIG. 5E illustrates another exemplary configuration of a vapor compression system 565, where phase separator 561 is disposed in the flow path between the electrochemical device 532 and the condenser 506. The system 565 can be configured such that, at a temperature and pressure in the phase separator 561, the carrier gas is in the vapor phase and separates from the HFO 562. The separated carrier gas 563 can be siphoned from the phase separator 561 and directed via input line 566 for reuse by the electrochemical compressor 532. The substantially-carrier-gas-free HFO 562 can then be output from the phase separator 561 to condenser 506 for heat transfer.

Figure 6A:
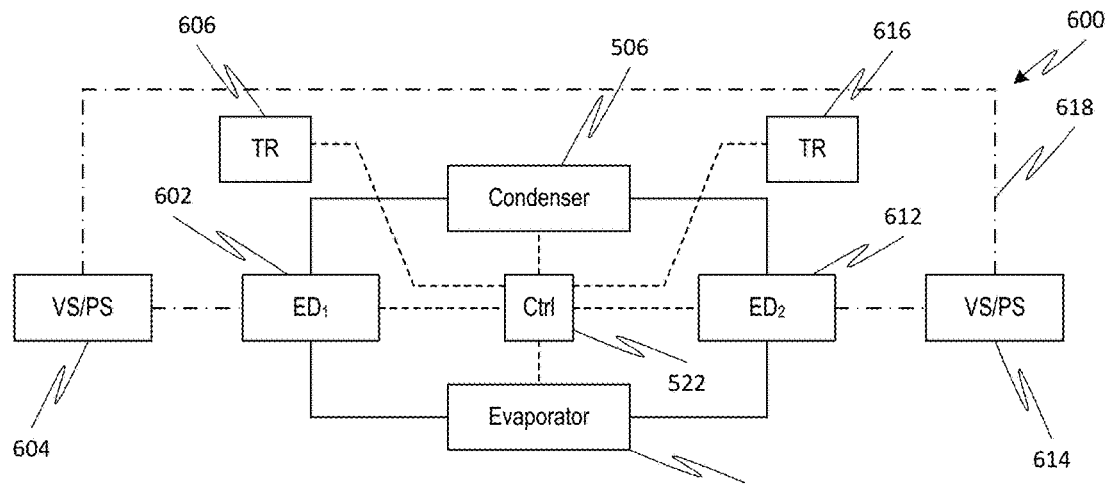
FIG. 6A is a simplified schematic diagram of an exemplary two-mode vapor compression system where electrochemical devices can switch between compression and expansion, according to one or more embodiments of the disclosed subject matter.
Figure 8:
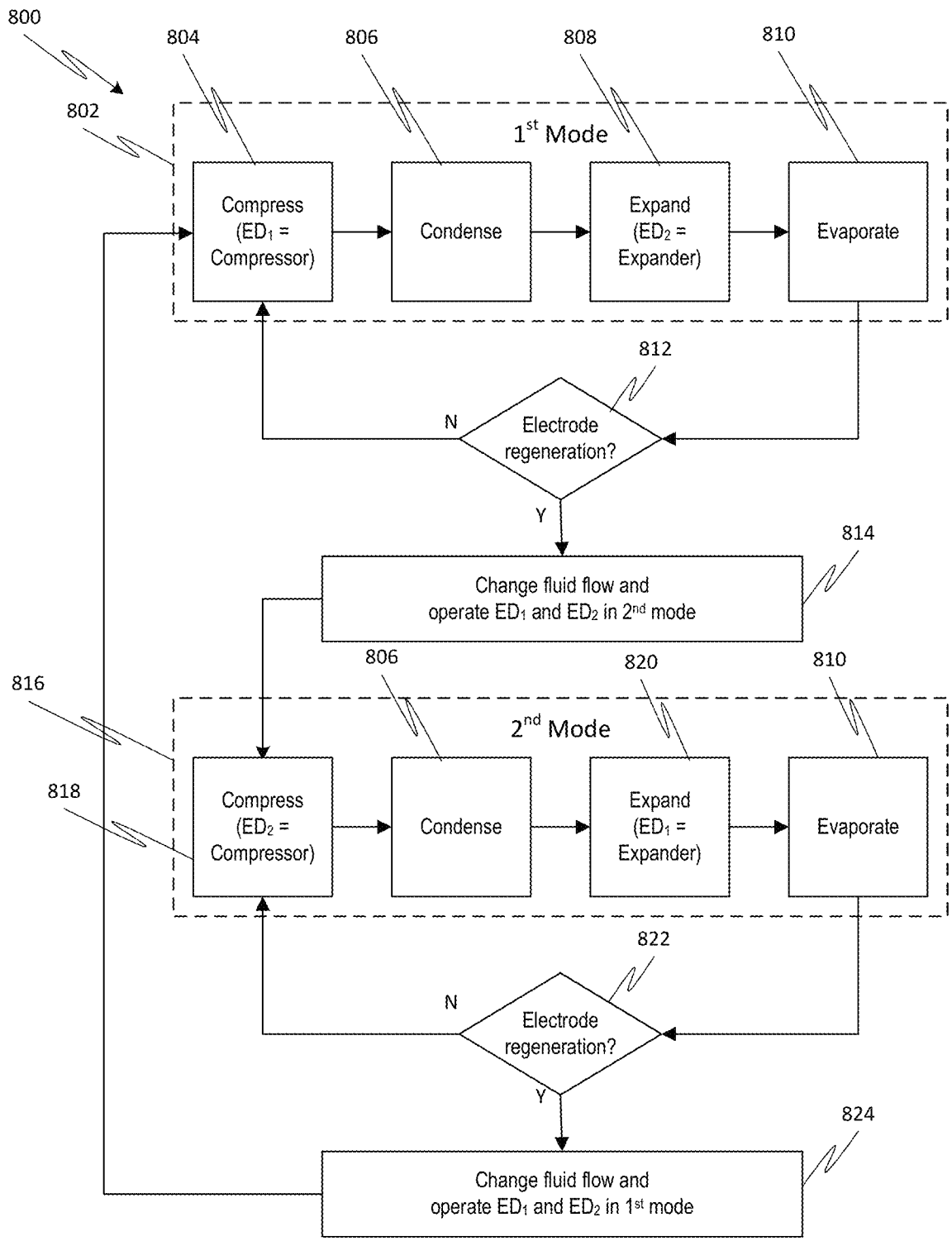
FIG. 8 is an exemplary process flow diagram for operation of a two-mode vapor compression system employing switchable electrochemical devices, according to one or more embodiments of the disclosed subject matter.

Alternatively or additionally, the carrier gas can be prevented from circulating in the vapor compression system by constructing each electrochemical device with carrier-gas-absorbing electrodes. The electrochemical devices can switch between operation as either a compressor or power-harvesting evaporator, depending on its mode of operation. For example, FIG. 6A shows a compression system 600 with a first electrochemical device 602 in a flow path between the evaporator 518 and the condenser 506, and a second electrochemical device 612 in a complementary flow path between the condenser 506 and the evaporator 518. FIG. 8 describes operation 800 of the compression system 600 in a first mode 802 and a second mode 816.

The electrodes of the MEA in each electrochemical device 602, 612 can be formed, or having a coating, of metal hydride so as to store the $H_2$ carrier gas therein and prevent $H_2$ from circulating in the vapor compression cycle outside of the respective MEA. Each electrochemical device 602, 612 can have a respective power module 604, 614, which is switchable between a power supply mode and a power storage mode, and a respective thermal regulation unit 606, 616 for removing heat during respective compression and/or expansion processes. A power line 618 can electrically connect the power modules 604, 614 together so as to share electrical power therebetween.

Figure 6B:
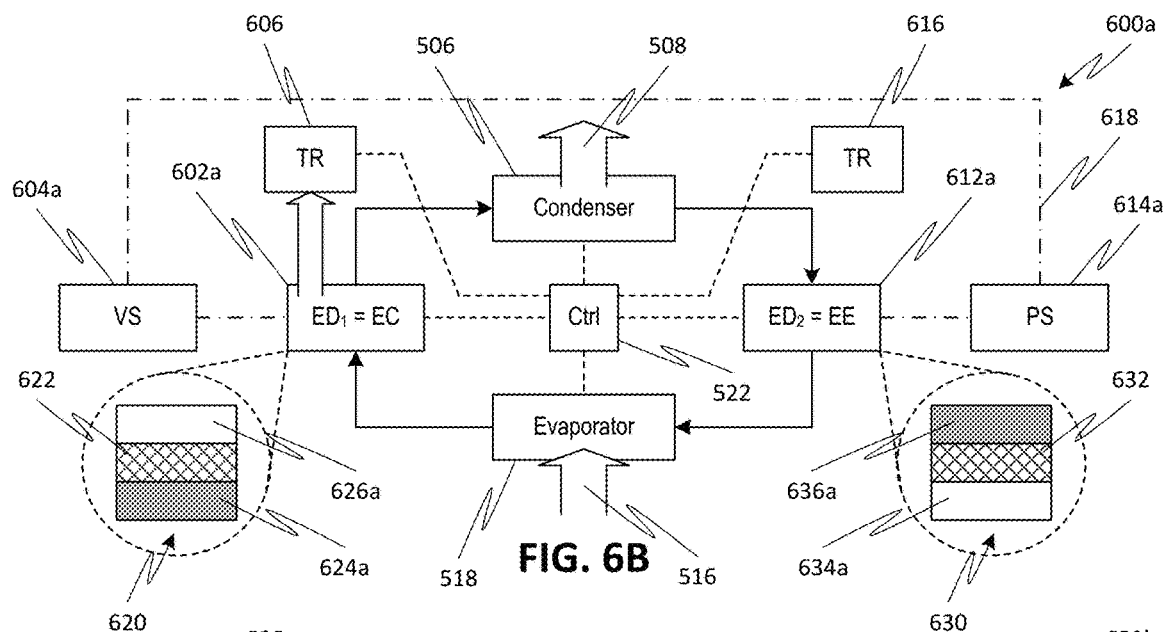
FIGS. 6B-6C illustrate exemplary first and second modes of operation for the system of FIG. 6A, according to one or more embodiments of the disclosed subject matter.

In a first mode 600a of operation illustrated in FIG. 6B (802 in FIG. 8), the flow of HFO working fluid is in a clockwise direction, with the first electrochemical device 602a operating as compressor and the second electrochemical device 612a operating as expander. The first power module 604a thus acts as a voltage source for the electrochemical compressor 602a, while the second power module 614a acts a power storage for the electrochemical expander 612a.

The compression 804 of HFO working fluid by compressor 602a may be in a similar manner as described above with respect to FIG. 7A. For example, during the first mode 600a, at the anode 624a of the MEA 620 of the electrochemical compressor 602a, the HFO working fluid electrochemically reacts with hydrogen in the metal hydride of anode 624a to produce the HFO cation. The HFO cation is transferred across the PEM 622 to cathode 626a, where the cation is electrochemically dissociated back to HFO and hydrogen. At the cathode 626a, the hydrogen reacts with the material of the cathode to form metal hydride.

The compressed HFO working fluid is conveyed to condenser 506, where heat transfer causes condensation 806 of the HFO working fluid. The condensed HFO working fluid is conveyed to expander 612a. During the first mode 600a, the expansion 808 of HFO working fluid by expander 612a may be in a similar manner as described above with respect to FIG. 7B (i.e., the reverse operation from that of compressor 602a). For example, during the first mode 600a, at the cathode 636a of the MEA 630 of the electrochemical expander 612a, the HFO working fluid electrochemically reacts with hydrogen in the metal hydride of cathode 636a to produce the HFO cation. The HFO cation is transferred across the PEM 632 to anode 634a, where the cation is electrochemically dissociated back to HFO and hydrogen. At the anode 634a, the hydrogen reacts with the material of the anode to form metal hydride. The expanded HFO working fluid is conveyed to evaporator 518, where heat transfer causes evaporation 810 of the HFO working fluid.

At the beginning of the first mode 600a, the anode 624a has substantially all of the hydrogen in MEA 620 (i.e., is fully charged with hydrogen), while the cathode 626b has substantially none of the hydrogen (i.e., is fully discharged). Similarly, at the beginning of the first mode 600a, the cathode 636a has substantially all of the hydrogen in MEA 630, while the anode 634a has substantially none of the hydrogen. The processes of the first mode 600a can continue until the inlet electrodes (i.e., anode 624a of compressor 602a and cathode 636a of expander 612a) are fully discharged, i.e., all of the hydrogen therein has been transferred through their respective PEM 622, 632 to charge the corresponding outlet electrodes (i.e., cathode 626a of compressor 602a and anode 634a of expander 612a). Thus, at 812, the process 800 can determine if regeneration of electrodes is required.

Once the inlet electrodes 624a, 636a have been fully discharged (i.e., depleted of hydrogen), system 600 can switch to a second mode at 814. In the second mode 600b of operation, illustrated in FIG. 6C, the flow of HFO working fluid is reversed from the first mode 600a, i.e., flows in a counter-clockwise direction, and/or the polarity of the electrochemical devices can be reversed. In addition, the first electrochemical device 602b is reconfigured to operate as an expander while the second electrochemical device 612b is reconfigured to operate as a compressor. The first power module 604b thus acts as a power storage for the electrochemical expander 602b, and the second power module 614b acts as a voltage source for the electrochemical compressor 612b. In effect, the reversed flow and/or polarity of the second mode 600b is equivalent to the first and second electrochemical devices 602a, 612a switching places in the first mode 600a.

Thus, the compression 818 of HFO working fluid by compressor 612b may be in a manner similar to that described above with respect to FIG. 7A, while the expansion 820 by expander 602b may be in a manner similar to that described above with respect to FIG. 7B. At the beginning of the second mode 600b, the anode 634b of the electrochemical compressor 612b has substantially all of the hydrogen MEA 620 (e.g., having been charged with hydrogen during the first mode 600a), while the cathode 636b has substantially none of the hydrogen (e.g., having been discharged of hydrogen during the first mode 600a). Similarly, at the beginning of the second mode 600b, the cathode 626b has substantially all of the hydrogen in MEA 620, while the anode 624b has substantially none of the hydrogen. The processes of the second mode 600b can continue until the inlet electrodes (i.e., anode 634b of compressor 612b and cathode 626b of expander 602b) are fully discharged. Thus, at 822, the process 800 can determine if regeneration of electrodes is required. If so, the process 800 can switch system 600 back to the first mode of operation at 824. Such switching between first and second modes may be controlled by controller 522, for example, by monitoring the inlet or outlet electrodes of the electrochemical devices 602, 612 to determine a charge/discharge state thereof. The system 600 can thus repeatedly switch between first and second modes of operation to take advantage of the hydrogen charging status of the electrodes of the MEA of the electrochemical devices 602, 612.

Although 804-810 of the first mode are illustrated separately and 818, 806, 820, and 810 of the second mode are illustrated separately in FIG. 8, it is contemplated that such process steps may occur contemporaneously in each respective mode, for example, during the continuous operation of a vapor compression cycle in that respective mode. Moreover, the particular order of 804-810 and 818, 806, 820, and 810 in FIG. 8 has been chosen for explanatory purposes only and is not intended to be limiting. Indeed, in practical embodiments of the disclosed subject matter, the illustrated steps may occur before or during other steps.

Figure 6C:
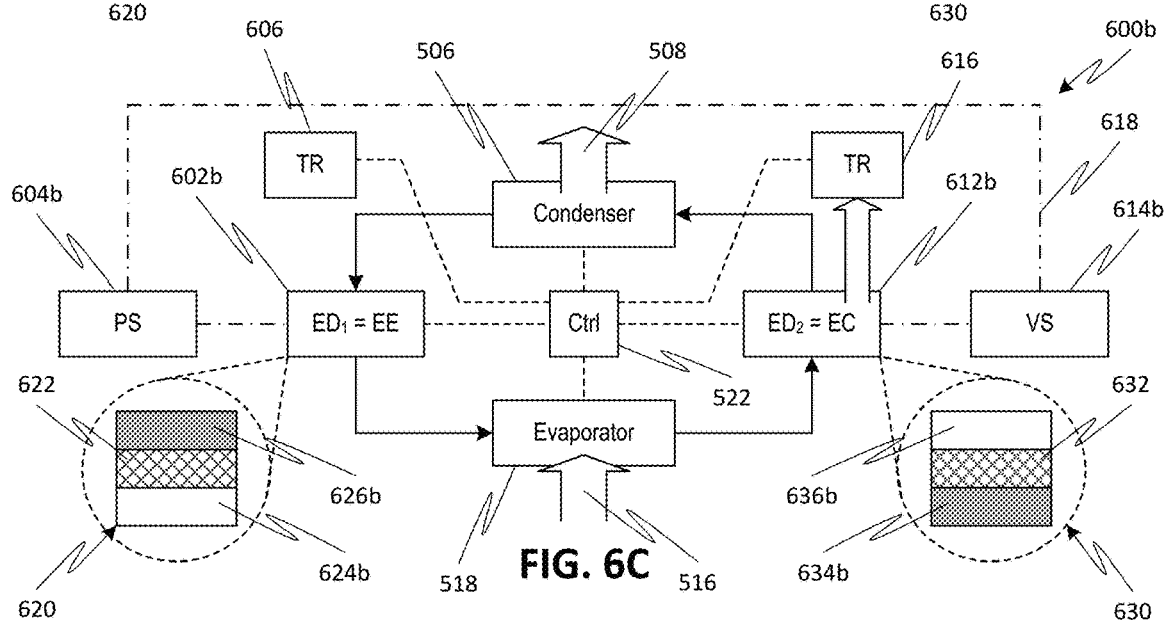

Although FIGS. 6B-6C indicate that the flow through the condenser 506 and evaporator 518 are reversed when switching between first mode 600a and second mode 600b, it is also possible that the flow direction through the heat exchangers 506, 518 may be kept the same regardless of the operating mode, according to one or more contemplated embodiments. Indeed, the HFO working fluid flow to/from each heat exchanger 506, 518 may be rerouted via appropriate switches, valves, and/or other flow channels to achieve the same effect of switching between first 600a and second 600b modes without otherwise altering the flow of HFO working fluid through the respective heat exchanger 506, 518.

Figure 6D:
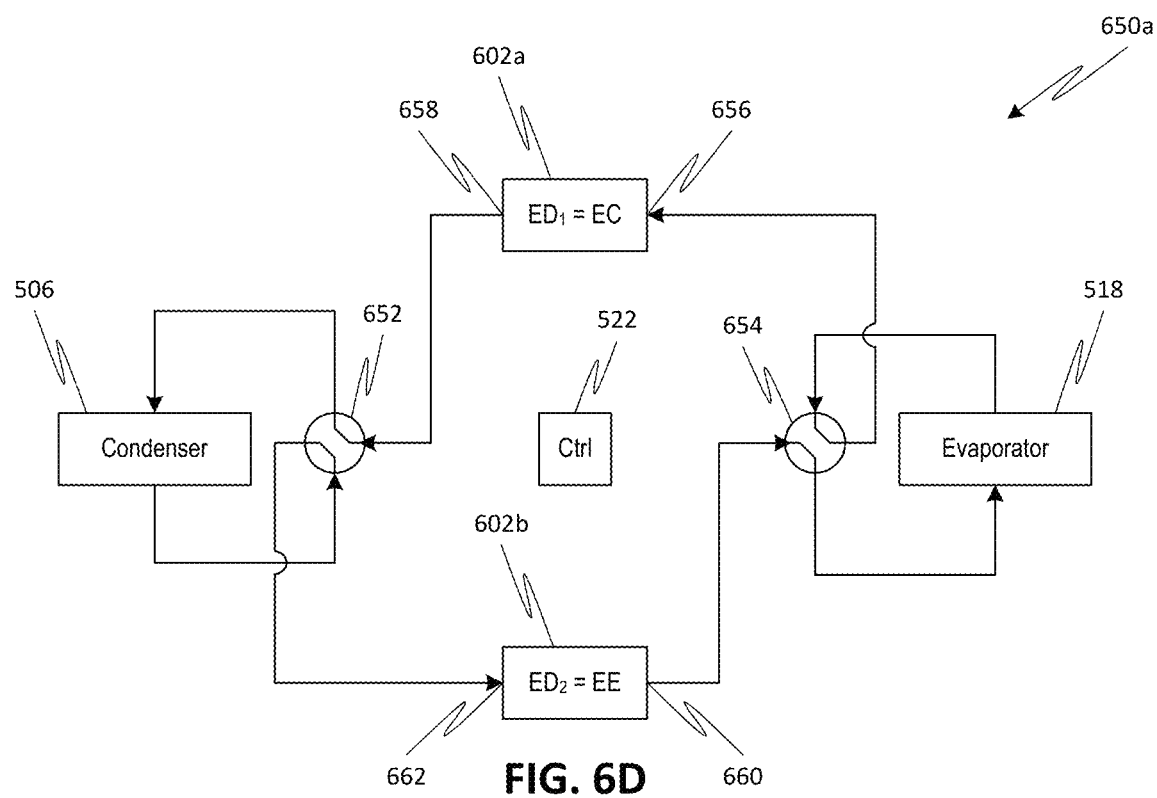
FIGS. 6D-6E illustrate exemplary first and second modes of operation of another exemplary two-mode vapor compression system, according to one or more embodiments of the disclosed subject matter.
Figure 6E:
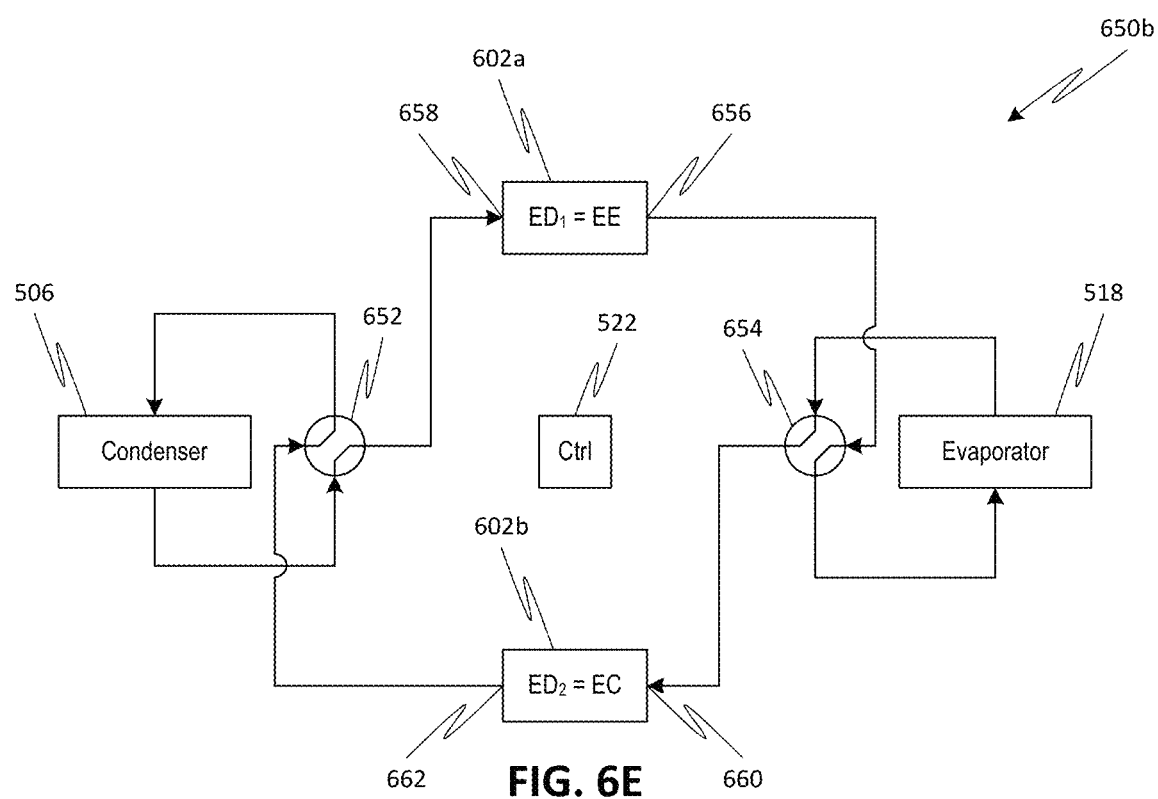

For example, FIGS. 6D-6E illustrate an exemplary setup for a system where the direction of flow of working fluid through heat exchangers 506, 518 is maintained regardless of the mode of operation 650a, 650b. The system can include a first valve 652 for routing flow to/from condenser 506 and a second valve 654 for routing flow to/from evaporator 518. For example, each valve 652, 654 can be a 4-way valve.

In a first mode 650a, the first electrochemical device 602a operates as compressor while the second electrochemical device 602b operates as expander. Valve 652 is at a first orientation that routes discharge from port 658 of the first electrochemical device 602a to the inlet of condenser 506, and that routes discharge from the condenser 506 to port 662 of the second electrochemical device 602b. Valve 654 is at a first orientation that routes discharge from port 660 of the second electrochemical device 602b to the inlet of evaporator 518, and that routes discharge from the evaporator to port 656 of the first electrochemical device 602a. In effect, the first mode 650a may operate similar to the first mode 600a of FIG. 6B, with the mode continuing until inlet electrodes of the respective electrochemical devices 602a, 602b are exhausted.

Once the inlet electrodes have been exhausted (or when regeneration of electrodes is otherwise desired), the system can switch to the second mode 650b, as illustrated in FIG. 6E. In particular, valve 652 changes to a second orientation that routes discharge from condenser 506 to port 658 of the first electrochemical device 602a, and that routes discharge from port 662 of the second electrochemical device 602b to the inlet of the condenser 506. Valve 654 changes to a second orientation that routes discharge from the evaporator to port 660 of the second electrochemical device 602b, and that routes discharge from port 656 of the first electrochemical device 602a to the inlet of evaporator 518. In the second mode 650b, the first electrochemical device 602a and the second electrochemical device 602b operate as expander and compressor, respectively. In effect, the second mode 650b may operate similar to the second mode 600b of FIG. 6C, with the mode continuing until inlet electrodes of the respective electrochemical devices 602a, 602b, are exhausted.

As compared to the first mode 650a, the direction of flow of the working fluid through the electrochemical devices 602a, 602b in the second mode 650b has been reversed. Moreover, the functions of the electrochemical devices 602a, 602b have been switched. Thus, the first electrochemical device 602a serves as compressor in the first mode 650a and as expander in the second mode 650b, and vice versa for the second electrochemical device 602b. However, the direction of working fluid flow through the condenser 506 and evaporator 518 remains the same regardless of operation mode 650a, 650b.

Figure 6F:
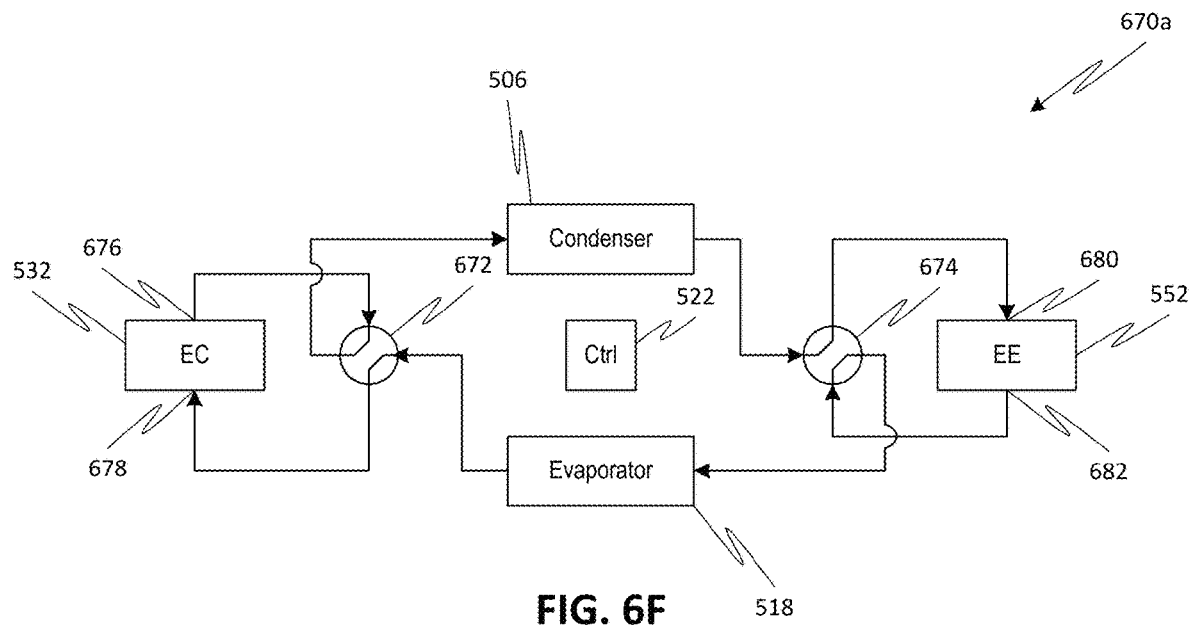
FIGS. 6F-6G illustrate exemplary first and second modes of operation of yet another exemplary two-mode vapor compression system, according to one or more embodiments of the disclosed subject matter.
Figure 6G:
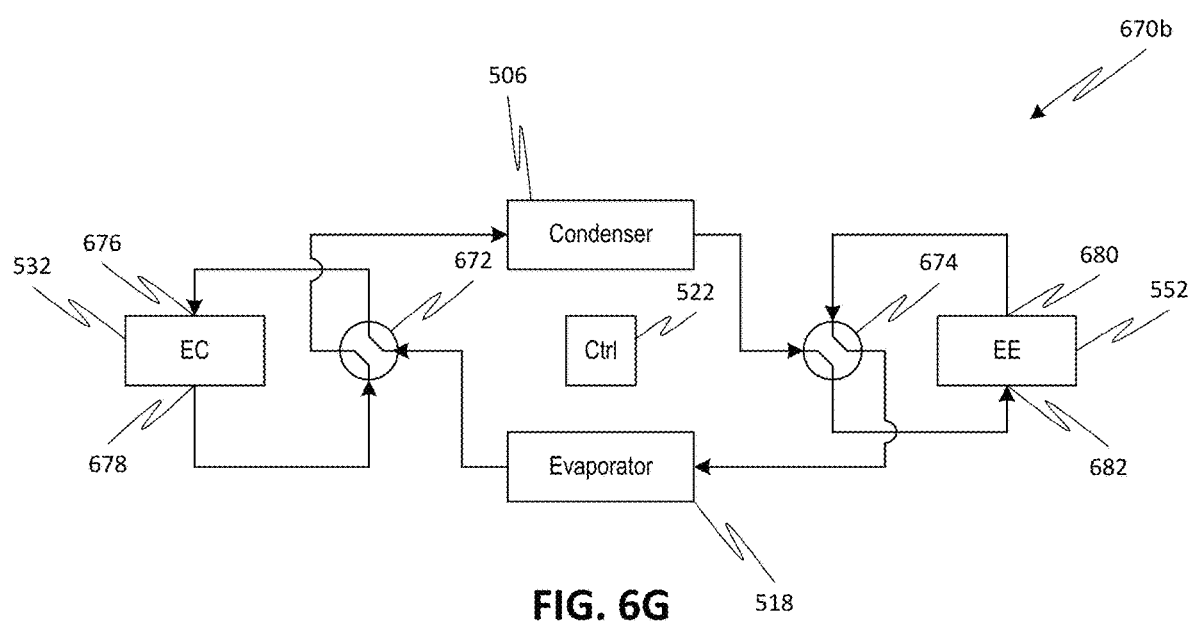

Other configurations for regeneration of hydrogen storage electrodes in electrochemical devices are also possible according to one or more contemplated embodiments. For example, FIGS. 6F-6G illustrate an exemplary setup for a system where the direction of working fluid flow through the electrochemical devices 532, 552 is reversed to regenerate the electrodes while maintaining the respective functions of the electrochemical devices 532, 552. The system can include a first valve 672 for routing flow to/from the electrochemical compressor 532 and a second valve 674 for routing flow to/from the electrochemical evaporator 552. For example, each valve 672, 674 can be a 4-way valve.

In a first mode 670a, valves 672, 674 are in a respective first orientation. Thus, valve 672 routes working fluid discharged from port 676 of compressor 532 to the inlet of condenser 506, and routes working fluid discharged from evaporator 518 to port 678 of compressor 532. Valve 674 routes working fluid discharged from port 682 of expander 552 to the inlet of evaporator 518, and routes working fluid discharged from condenser 506 to port 680 of expander 552. In effect, the first mode 670a may operate similar to the first mode 600a of FIG. 6B, with the mode continuing until inlet electrodes of the respective compressor 532 and evaporator 552 are exhausted.

Once the inlet electrodes have been exhausted (or when regeneration of electrodes is otherwise desired), the system can switch to the second mode 670b, as illustrated in FIG. 6G. In particular, valves 672, 674 change to respective second orientations, so as to reverse a direction of the flow through electrochemical devices 532, 552. However, unlike the second mode 650b of FIG. 6B, the electrochemical devices of the second mode 670b continue to process the working fluid in the same manner as the first mode 670a, i.e., device 532 as compressor and device 552 as expander. In effect, the second mode 670b may operate similar to the second mode 600b of FIG. 6C, with the mode continuing until inlet electrodes of the respective electrochemical devices 532, 552 are exhausted.

In another example of a system for electrode regeneration, an electrochemical module may have a pair of electrochemical devices that operate in an alternating manner to provide a particular thermodynamic process (e.g., electrochemical module acting as a compressor). When the anode of a first of the electrochemical devices becomes depleted, the system may switch the HFO working fluid input to the second electrochemical device. A polarity of the electric field applied to the first electrochemical device can then be switched to allow regeneration of the input electrode while the second electrochemical device actively performs compression of the HFO working fluid. The system may switch back and forth, redirecting HFO working fluid input between the pair of electrochemical devices, such that one is always performing compression while the other is idle/recharging.

Figure 9A:
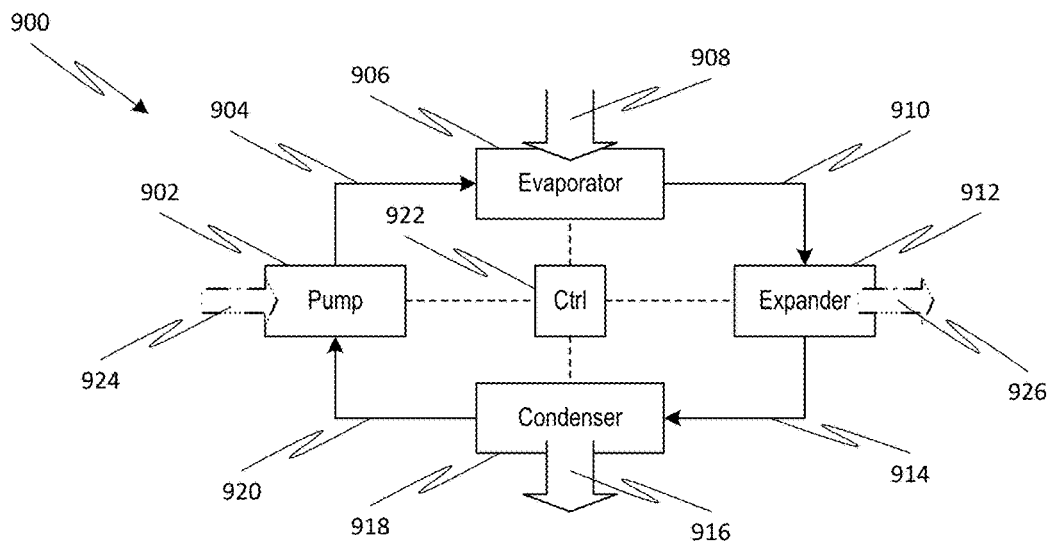
FIG. 9A is a simplified schematic diagram of an organic Rankine cycle (ORC) where an electrochemical device can be employed as one or more components, according to one or more embodiments of the disclosed subject matter.

As noted above, embodiments of the disclosed electrochemical device can be employed in a power generation system, such as an organic Rankine cycle (ORC) or a Brayton cycle. For example, FIG. 9A illustrates an exemplary configuration of ORC 900, which may have a substantially conventional configuration other than the use of the electrochemical device(s) and HFO as working fluid. For example, ORC 900 can have a heat exchanger 506 operating as evaporator, which transfers heat 908 to the working fluid circulating therethrough, and a heat exchanger 918 operating as a condenser, which transfers heat 916 from the working fluid circulating therethrough. A controller 922 can be operatively coupled to the different components of the ORC 900 to control operation and performance of the system, for example, to achieve a desired net power output 926.

In ORC 900, the pump 902 (e.g., a conventional liquid pump or electrochemical device) receives liquid-phase HFO at 920 from condensing heat exchanger 918 and pumps it to a higher pressure at 904. Heat 908 is transferred to the pumped HFO 904 via heat exchanger 906 to generate vapor-phase HFO at 910. After evaporating heat exchanger 906, the vapor-phase HFO 910 is provided to an expansion device 912 (e.g., a turbine or electrochemical device), which generates power 926 by expanding the HFO (a portion of which may be used as power 924 for pump 902). Heat 916 is transferred from the resulting low pressure HFO 914 using condensing heat exchanger 918. The resulting liquid-phase HFO at 920 can then be conveyed to pump 902, where the cycle repeats. Heat 908 can thus be used to generate a net power output 926.

Figure 9B:
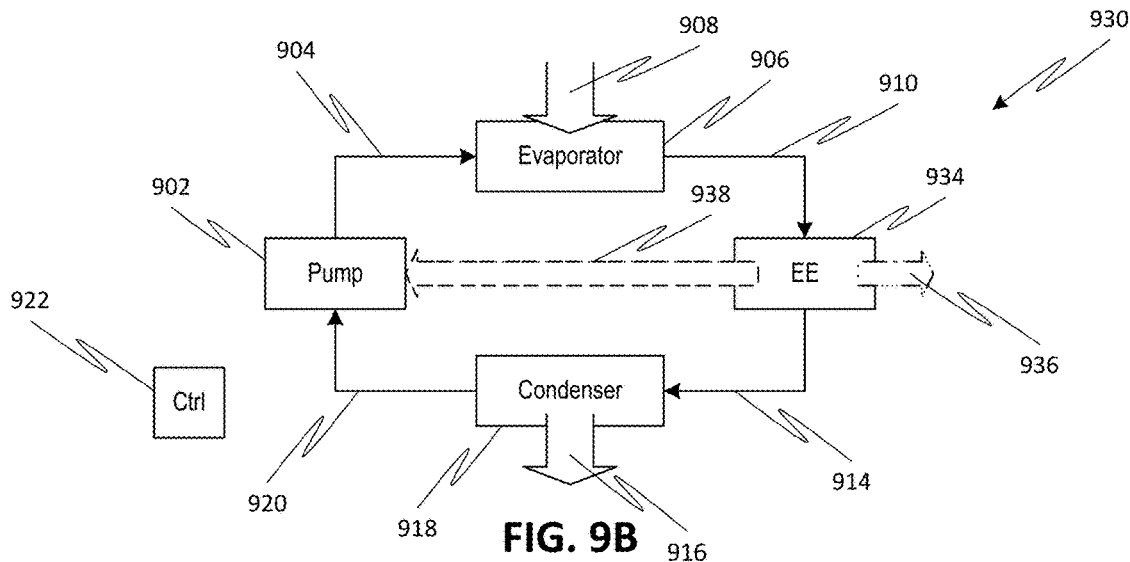
FIG. 9B illustrates an exemplary configuration of the system of FIG. 9A where an electrochemical device is used as expander, according to one or more embodiments of the disclosed subject matter.
Figure 9C:
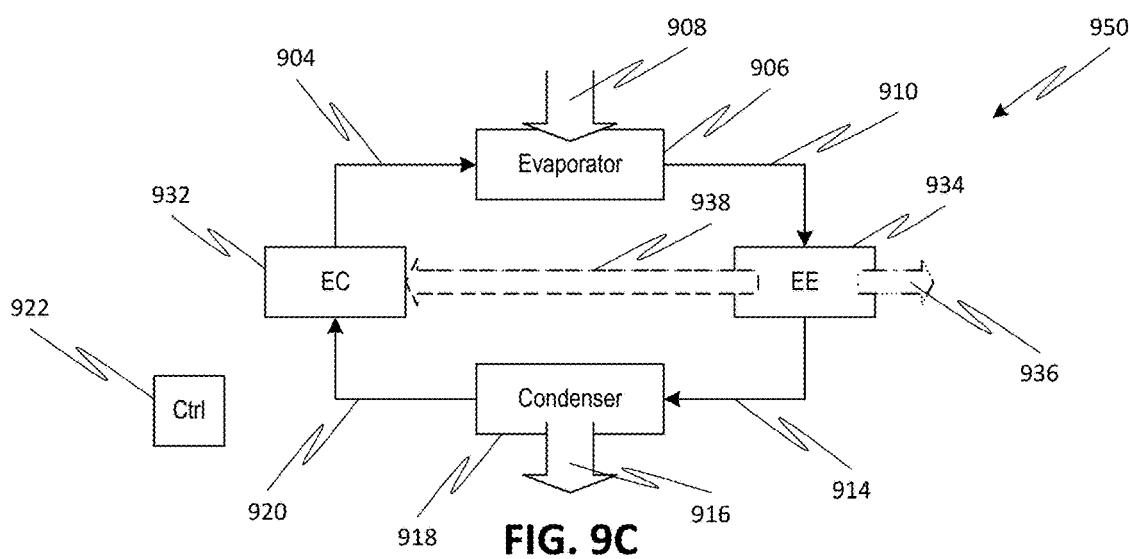
FIG. 9C illustrates an exemplary configuration of the system of FIG. 9A where electrochemical devices are used as pump and expander, respectively, according to one or more embodiments of the disclosed subject matter.

The electrochemical device may be employed as pump 902 and/or expander 912 in ORC 900. For example, FIG. 9B shows ORC 930 where an electrochemical device 934 operates as expander. The electrochemical expander 934 may be similar to the device illustrated in FIG. 1B and described above. Thus, as the HFO working fluid passes through the MEA of the electrochemical expander 934, electrical power may be harvested and used for powering different components of ORC 930. For example, at least part 938 of the harvested electrical power can be used to power pump 902. The remaining power 936 (i.e., net power) generated by the electrochemical expansion 934 can be directed for further processing (e.g., conversion of DC to AC voltage), use, or storage. Alternatively or additionally, the pump 902 of FIG. 9B can be replaced with an electrochemical device 932, for example, as shown in ORC 950 of FIG. 9C. For example, the electrochemical device 932 may be similar to the device illustrated in FIG. 1A and described above.

Figure 10A:
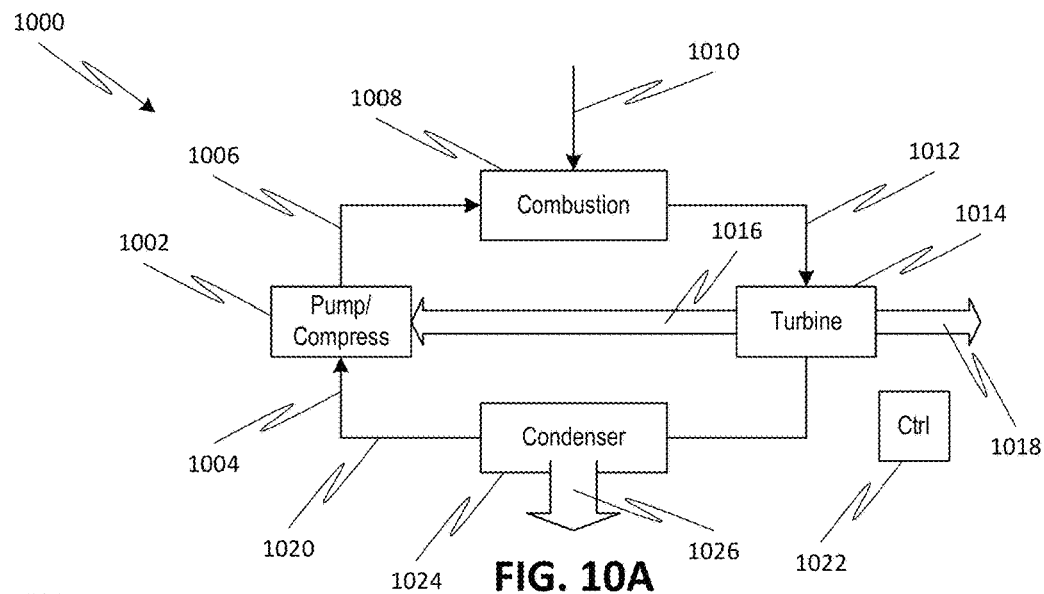
FIG. 10A is a simplified schematic diagram of Brayton cycle where an electrochemical device can be employed as one or more components, according to one or more embodiments of the disclosed subject matter.

FIG. 10A illustrates an exemplary configuration of a Brayton cycle 1000, which may have a substantially conventional configuration other than the use of the electrochemical device(s) and HFO as working fluid. For example, Brayton cycle 1000 can have a combustion chamber 1008 that receives pressurized working fluid 1006 from a pump or compressor 1002. Fuel 1010 is burned in combustion chamber 1008, which heats the working fluid therein and produces a heated, pressurized working fluid output 1012. The working fluid output 1012 is provided to a turbine or expander 1014, which expands the working fluid to extract useful work or power 1018 therefrom. A portion 1016 of the extracted power can be used to drive pump/compressor 1002. The expanded working fluid 1020 output from the expander 1014 can be rerouted directly back to the pump/compressor 1002 (not shown), or indirectly via a heat exchanger 1024 for rejecting heat 1026 from the working fluid 1020. A controller 1022 can be operatively coupled to the different components of the Brayton cycle 1000 to control operation and performance of the system, for example, to achieve a desired net power output 1018.

Figure 10B:
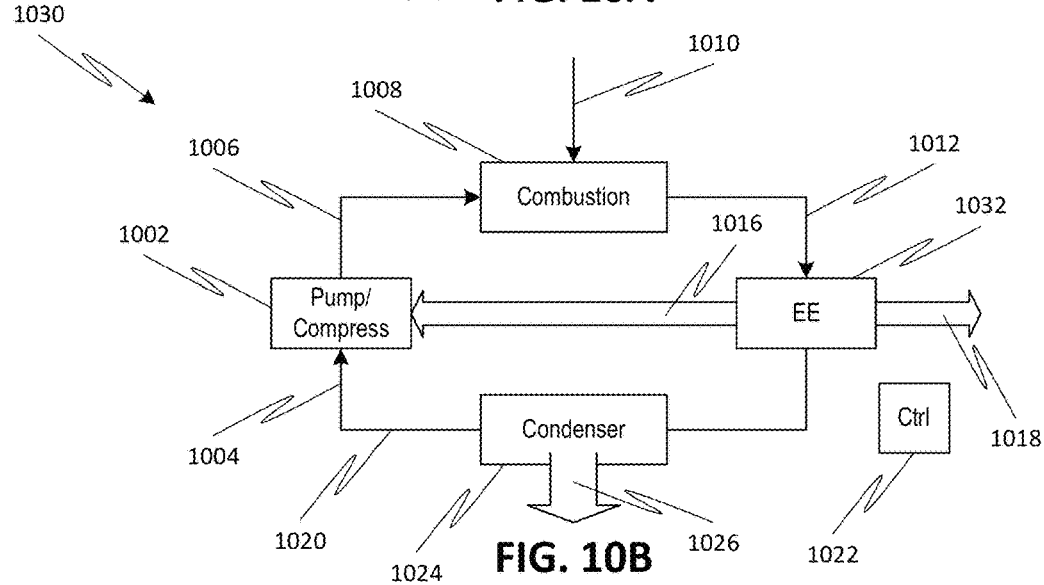
FIG. 10B illustrates an exemplary configuration of the system of FIG. 10A where an electrochemical device is used as expander, according to one or more embodiments of the disclosed subject matter.
Figure 10C:
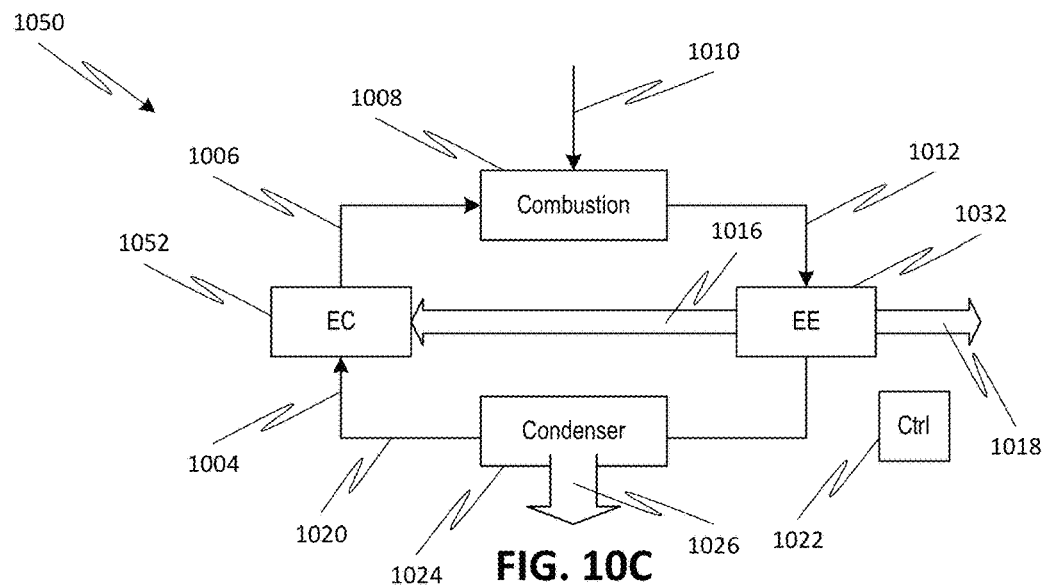
FIG. 10C illustrates an exemplary configuration of the system of FIG. 10A where electrochemical devices are used as pump and expander, respectively, according to one or more embodiments of the disclosed subject matter.

The electrochemical device may be employed as pump 1002 and/or expander 1014 in Brayton cycle 1000. For example, FIG. 10B shows Brayton cycle 1030 where an electrochemical device 1032 operates as expander. The electrochemical expander 1032 may be similar to the device illustrated in FIG. 1B and described above. Thus, as the HFO working fluid passes through the MEA of the electrochemical expander 1032, electrical power may be harvested and used for powering different components of Brayton cycle 1030. For example, at least part 1016 of the harvested electrical power can be used to power pump 1002. The remaining power 1018 (i.e., net power) generated by the electrochemical expansion 1032 can be directed for further processing (e.g., conversion of DC to AC voltage), use, or storage. Alternatively or additionally, the pump 1002 of FIG. 10B can be replaced with an electrochemical device 1052, for example, as shown in Brayton cycle 1050 of FIG. 10C. For example, the electrochemical device 1052 may be similar to the device illustrated in FIG. 1A and described above.

Although particular systems or cycles, in which the disclosed electrochemical devices can be used to provide pumping, compression, or expansion, have been described, embodiments of the disclosed subject matter are not limited thereto. Indeed, one of ordinary skill in the applicable arts will readily appreciate that the disclosed electrochemical devices can be provide pumping, compression, expansion, and/or power harvesting in other heating/cooling or power generation systems employing HFO beyond those specifically discussed herein. Moreover, aspects of the above described systems or cycles can be applied in isolation from other aspects thereof. For example, the electrochemical device may be used as a pump of HFO fluid, whether or not part of a heating/cooling or power generation system.

In addition, although particular configurations have been separately discussed above, the features of one particular configuration may apply to other configurations as well. For example, although FIGS. 6A-6G and 9A-10C do not specifically illustrate humidity sources (e.g., source 540 in FIGS. 5B-5E) for the electrochemical devices, such configurations can include humidity sources in a manner similar to that illustrated in FIGS. 5B-5E. Similarly, although FIGS. 6D-6G and 9A-10C do not specifically illustrate thermal regulation devices (e.g., device 536 in FIGS. 5B-5E) for the electrochemical devices, such configurations can include thermal regulation devices in a manner similar to that illustrated in FIGS. 5B-5E.

Although the description above has used the terms "fluid" and "working fluid," it will be readily apparent to one of ordinary skill in the applicable arts that such terminology includes the vapor and supercritical phases of the HFO refrigerant as well as the liquid phase. Moreover, although exemplary chemistries and materials have been discussed above, one of ordinary skill in the art will understand that the teachings of the present disclosure can be extended to other materials and chemistries. Thus, embodiments of the disclosed subject matter are not limited to the specific chemistries and materials discussed herein.

It will be appreciated that the aspects of the disclosed subject matter can be implemented, fully or partially, in hardware, hardware programmed by software, software instruction stored on a computer readable medium (e.g., a non-transitory computer readable medium), or any combination of the above.

For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

The terms "system," "device," "unit," and "module" have been used interchangeably herein, and the use of one term in the description of an embodiment does not preclude the application of the other terms to that embodiment or any other embodiment.

It is thus apparent that there is provided, in accordance with the present disclosure, systems, devices, and methods employing electrochemical processing of HFOs. Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A system comprising:
an electrochemical device; and
a fluid circulating in the system,
wherein the electrochemical device comprises a proton exchange membrane disposed between a pair of electrodes;
wherein the electrochemical device is constructed to transport the fluid through the proton exchange membrane, in the presence of an electric field applied between the pair of electrodes, via a combination of the fluid with a carrier gas,
wherein each of the pair of electrodes comprises a respective catalyst, and
wherein the carrier gas comprises $H_2$, and the fluid comprises a hydrofluoroolefin (HFO).

2. The system of claim 1, wherein the electrochemical device is constructed to transport the fluid through the proton exchange membrane such that pressure of the fluid at an outlet of the electrochemical device is different from that at an inlet of the electrochemical device.

3. The system of claim 1, wherein the system is constructed as a heating/cooling system, the fluid is a working fluid of the heating/cooling system, and the electrochemical device acts as one of a compressor and expander of the working fluid in the heating/cooling system.

4. The system of claim 1, wherein the system is constructed as a power generation system, the fluid is a working fluid of the power generation system, and the electrochemical device acts as one of a compressor, a pump, and an expander of the working fluid in the power generating system.

5. The system of claim 1, wherein the fluid reacts with the carrier gas at one of the electrodes to form a cation, the cation is transported through the proton exchange membrane, and the cation combines with electrons at the other of the electrodes to re-form the fluid and carrier gas.

6. The system of claim 1, comprising:
an electrochemical expander,
wherein the electrochemical expander comprises another proton exchange membrane disposed between another pair of electrodes, and
the electrochemical expander is constructed to transport the fluid through the another proton exchange membrane such that pressure of the fluid is reduced and power is generated between the another pair of electrodes.

7. The system of claim 6, wherein the power generated between the another pair of electrodes powers, at least in part, the pair of electrodes of the electrochemical device.

8. The system of claim 1, wherein:
the proton exchange membrane comprises an ionomer disposed between the pair of electrodes, and
the ionomer comprises a sulfonated tetrafluoroethylene-based fluoropolymer-copolymer.

9. The system of claim 1, wherein the catalyst comprises Pt or a metal hydride.

10. The system of claim 1, wherein the electrochemical device is constructed such that the carrier gas is prevented from circulating outside of the electrochemical device.

11. The system of claim 1, further comprising a controller that controls operation of the system,
wherein the controller is configured to periodically switch circulation of the fluid and control the electric field applied to the pair of electrodes, such that the electrochemical device switches function from one of compression and expansion to the other of compression and expansion.

12. A method comprising:
(a) applying an electric field between first and second electrodes, the first electrode being on an inlet side of a proton exchange membrane of an electrochemical module, the second electrode being on an outlet side of the proton exchange membrane, the outlet side being opposite to the inlet side,
(b) at the inlet side of the proton exchange membrane, combining a fluid and a carrier gas;
(c) under influence of the applied electric field, transporting the combined fluid and carrier gas through the proton exchange membrane to the outlet side; and
(d) at the outlet side of the proton exchange membrane, dissociating the transported combination to re-form the fluid and carrier gas,
wherein the first and second electrodes comprise a respective catalyst, and
wherein the carrier gas comprises $H_2$, and the working fluid comprises a hydrofluoroolefin (HFO).

13. The method of claim 12, wherein the transporting of (c) and dissociating of (d) are such that the fluid at the outlet side has a pressure higher than that of the fluid at the inlet side prior to the combining of (b).

14. The method of claim 12, wherein the fluid is in a liquid phase and the transporting of (c) is effective to pump the fluid.

15. The method of claim 12, wherein:
in (b), the fluid reacts with the carrier gas at the inlet side to form a cation,
in (c), the cation is transported through the proton exchange membrane, and
in (d), the cation combines with electrons at the outlet side to re-form the fluid and the carrier gas.

16. The method of claim 12, further comprising:
(e) conveying the fluid of (d) from the outlet side of the proton exchange membrane and transferring heat from the conveyed fluid so as to reduce a temperature and/or change a phase of the conveyed fluid;
(f) expanding the fluid from (e) so as to reduce a pressure thereof; and
(g) transferring heat to the fluid from (f) so as to increase a temperature and/or change a phase of the fluid, and conveying the fluid to the inlet side of the proton exchange membrane for (b),
wherein (a)-(g) are part of a vapor compression cycle.

17. The method of claim 16, wherein the expanding of (f) comprises transporting the fluid from (e) across another proton exchange membrane, thereby recapturing power expended in (a).

18. The method of claim 12, wherein:
the proton exchange membrane comprises an ionomer disposed between the first and second electrodes, and
the ionomer comprises a sulfonated tetrafluoroethylene-based fluoropolymer-copolymer.

19. The method of claim 12, wherein the carrier gas is retained within the electrochemical module by the first and second electrodes.

20. The method of claim 19, further comprising:
(h) regenerating the second electrode by reversing a polarity of the electric field applied between the first and second electrodes, such that carrier gas absorbed by the second electrode is released.

* * * * *